US012797056B2

(12) United States Patent
Carr

(10) Patent No.: US 12,797,056 B2
(45) Date of Patent: Nov. 17, 2026

(54) SPINAL RETRACTOR BLADE AND RELATED RETRACTOR DEVICE AND METHOD

(71) Applicant: James B. Carr, Atascadero, CA (US)

(72) Inventor: James B. Carr, Atascadero, CA (US)

(73) Assignee: James B. Carr, Atascadero, CA (US)

( * ) Notice: Subject to any disclaimer, the term of this patent is extended or adjusted under 35 U.S.C. 154(b) by 225 days.

(21) Appl. No.: 18/564,146

(22) PCT Filed: May 26, 2022

(86) PCT No.: PCT/US2022/031108
§ 371 (c)(1),
(2) Date: Nov. 27, 2023

(87) PCT Pub. No.: WO2022/251478
PCT Pub. Date: Dec. 1, 2022

(65) Prior Publication Data

US 2024/0245395 A1 Jul. 25, 2024

Related U.S. Application Data

(60) Provisional application No. 63/322,042, filed on Mar. 21, 2022.

(51) Int. Cl.
*A61B 17/02* (2006.01)
*A61B 17/56* (2006.01)
(Continued)

(52) U.S. Cl.
CPC ...... *A61B 17/0206* (2013.01); *A61B 17/7074* (2013.01); *A61F 2/4611* (2013.01); *A61B 2017/0256* (2013.01); *A61B 2017/564* (2013.01)

(58) Field of Classification Search
CPC .................................................. A61B 17/0206
See application file for complete search history.

(56) References Cited

U.S. PATENT DOCUMENTS 1,441,298 A 1/1923 Pineiro
4,694,826 A 9/1987 Chester
(Continued)

FOREIGN PATENT DOCUMENTS

WO 2010020257 A1 2/2010

OTHER PUBLICATIONS

Casha et al. "External rib structure can be predicted using mathematical models: An anatomical study with application to understanding fractures and intercostal muscle function," 2015, Clinical Anatomy, 28, 512-519 (Year: 2015).*
(Continued)

*Primary Examiner* — Christian A Sevilla
(74) *Attorney, Agent, or Firm* — Dominic A. Frisina

(57) ABSTRACT

A spinal retractor blade and retractor device are provided. The retractor blade may include an optional straight first leg having an end joined to an end of a shank. The blade further includes a transition extending from the straight first leg by about 90° to 180° and terminating in a free end. A width of the transition is suitable for receiving a spinous process. Retractors in accordance with the invention may optionally include a pair of such blades, and the blades themselves may optionally include a second straight leg between the transition and the free end. The legs of such blades may be non-parallel.

8 Claims, 23 Drawing Sheets

(51) Int. Cl.
*A61B 17/70* (2006.01)
*A61F 2/46* (2006.01)

(56) References Cited

U.S. PATENT DOCUMENTS

| | | | | |
|---|---|---|---|---|
| 4,754,746 | A | 7/1988 | Cox | |
| 5,795,291 | A | 8/1998 | Koros et al. | |
| 5,879,291 | A | 3/1999 | Kolata | |
| 6,241,659 | B1 * | 6/2001 | Bookwalter | A61B 17/0293 600/233 |
| 6,296,609 | B1 * | 10/2001 | Brau | A61B 17/02 600/210 |
| 6,551,316 | B1 | 4/2003 | Rinner et al. | |
| 6,648,891 | B2 | 11/2003 | Kim | |
| 7,210,485 | B2 | 5/2007 | Zinkel | |
| 7,842,074 | B2 | 11/2010 | Abdou | |
| 7,909,846 | B1 * | 3/2011 | Taylor | A61B 17/0206 606/198 |
| 8,801,757 | B2 | 8/2014 | Abdou | |
| 8,900,137 | B1 | 12/2014 | Lovell et al. | |
| 9,364,631 | B2 | 6/2016 | Tylke | |
| 9,662,150 | B1 | 5/2017 | Abdou | |
| 9,795,370 | B2 | 10/2017 | O'Connell | |
| 10,080,590 | B2 | 9/2018 | Abdou | |
| 10,448,941 | B2 | 10/2019 | Daavettila et al. | |
| 2004/0024291 | A1 | 2/2004 | Zinkel | |
| 2006/0264968 | A1 | 11/2006 | Frey et al. | |
| 2007/0213596 | A1 | 9/2007 | Hamada | |
| 2008/0255567 | A1 | 10/2008 | Accordino | |
| 2009/0036746 | A1 * | 2/2009 | Blackwell | A61B 17/0206 600/219 |
| 2010/0241128 | A1 | 9/2010 | Falabee | |
| 2010/0331849 | A1 | 12/2010 | Riesinger | |
| 2011/0066186 | A1 | 3/2011 | Michael et al. | |
| 2012/0101506 | A1 * | 4/2012 | Shim | A61B 17/0206 606/86 A |
| 2012/0226315 | A1 | 9/2012 | Altarac et al. | |
| 2013/0012998 | A1 | 1/2013 | Altarac et al. | |
| 2018/0008429 | A1 | 1/2018 | Li et al. | |
| 2018/0103941 | A1 | 4/2018 | Khan | |
| 2019/0021716 | A1 | 1/2019 | Waugh et al. | |
| 2020/0253595 | A1 | 8/2020 | McBride, Jr. | |

OTHER PUBLICATIONS

Angled Adson Cerebellar Retractors, Life Instruments, https://lifeinstruments.com/product/angled-adson-cerebellar-retractors/ at p. 1 of 1 (retrieved from the Internet Dec. 10, 2020).

Spine Instruments, Innomed Orthopedic Instruments, www.innomed.net/spine.htm#DeepTissueSpine at p. 29 of 35 (retrieved from the Internet Dec. 10, 2020).

Spine/Trauma Deep Tissue Retractor (product brochure), Innomed Orthopedic Instruments, http://www.innomed.net/PDFsInnomed/InnoDeepTissueSpTrRetractors.pdf at p. 1 of 1 (retrieved from the Internet Dec. 10, 2020).

Caspar Edward William Aylott, et al., Spinous process morphology: the effect of ageing through adulthood on spinous process size and relationship to sagittal alignment, European Spine Journal (2012) 21, pp. 1007-1012, Published by Springer-Verlag, 2011.

International Search Report dated Oct. 13, 2022 issued in PCT/US2022/31108.

Written Opinion dated Oct. 13, 2022 issued in PCT/US2022/31108.

International Preliminary Report on Patentability dated Nov. 21, 2023 issued in PCT/US2022/31108.

Merriam-Webster, "Segment", Definition of the word Segment.

Merriam-Webster, "Clip", Definition of the word Clip.

* cited by examiner

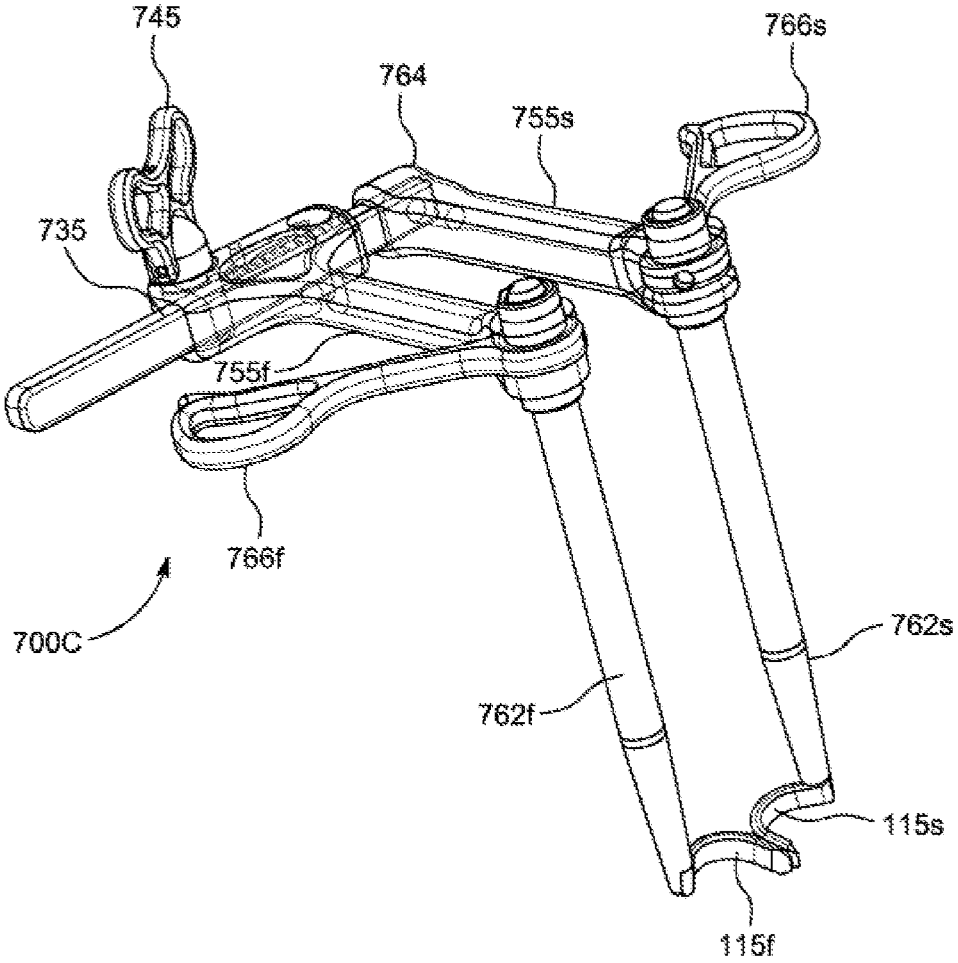
FIG. 7C1

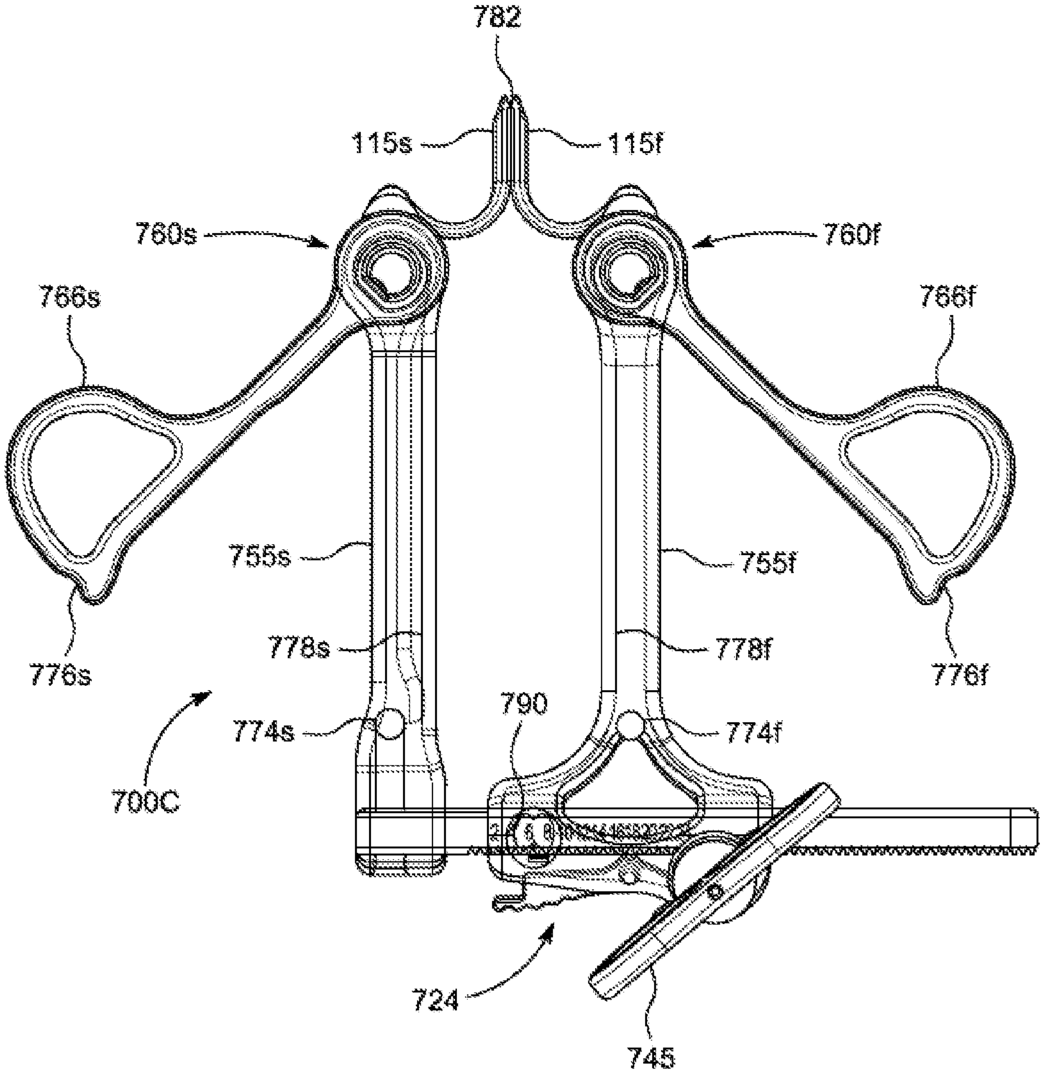
FIG. 7C2

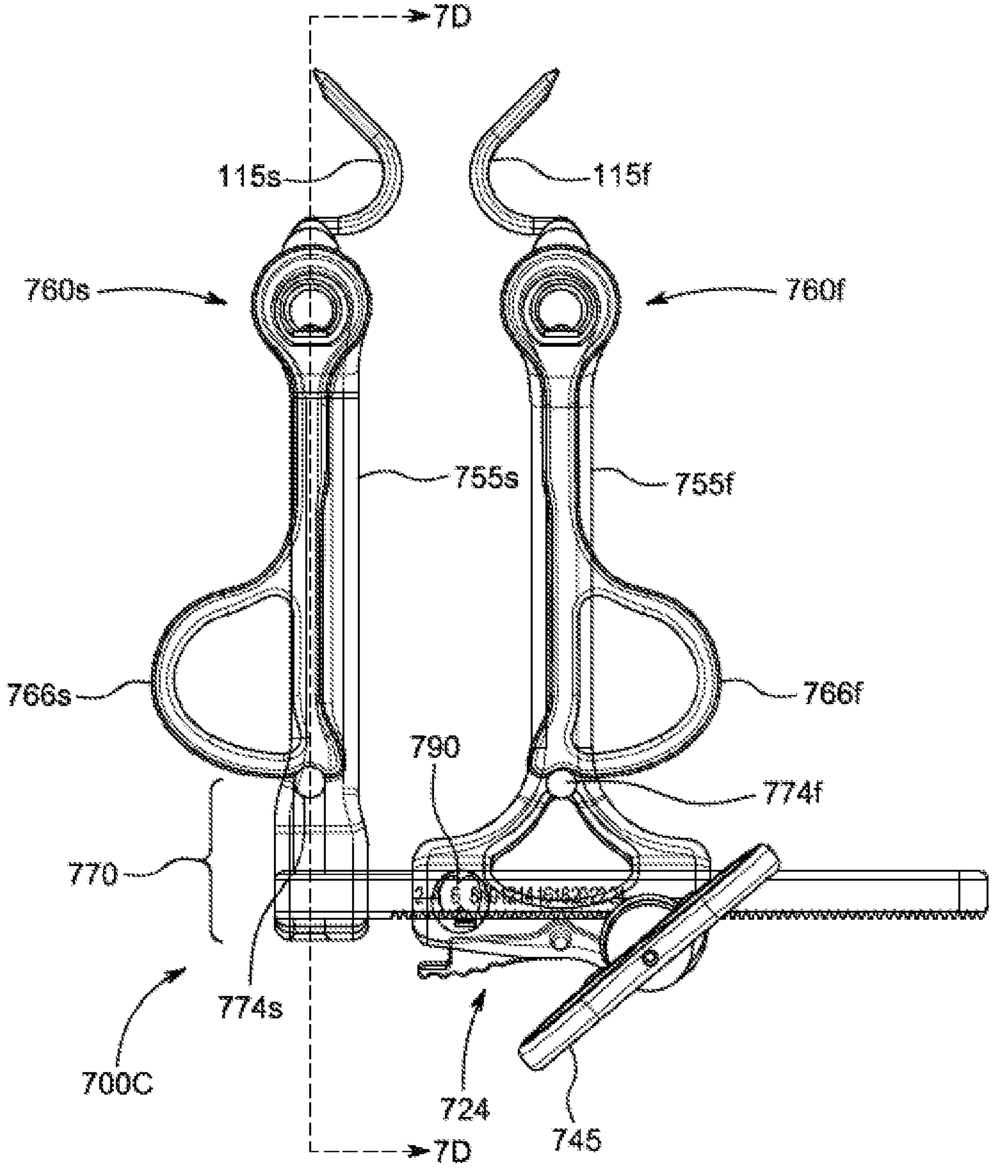
FIG. 7C3

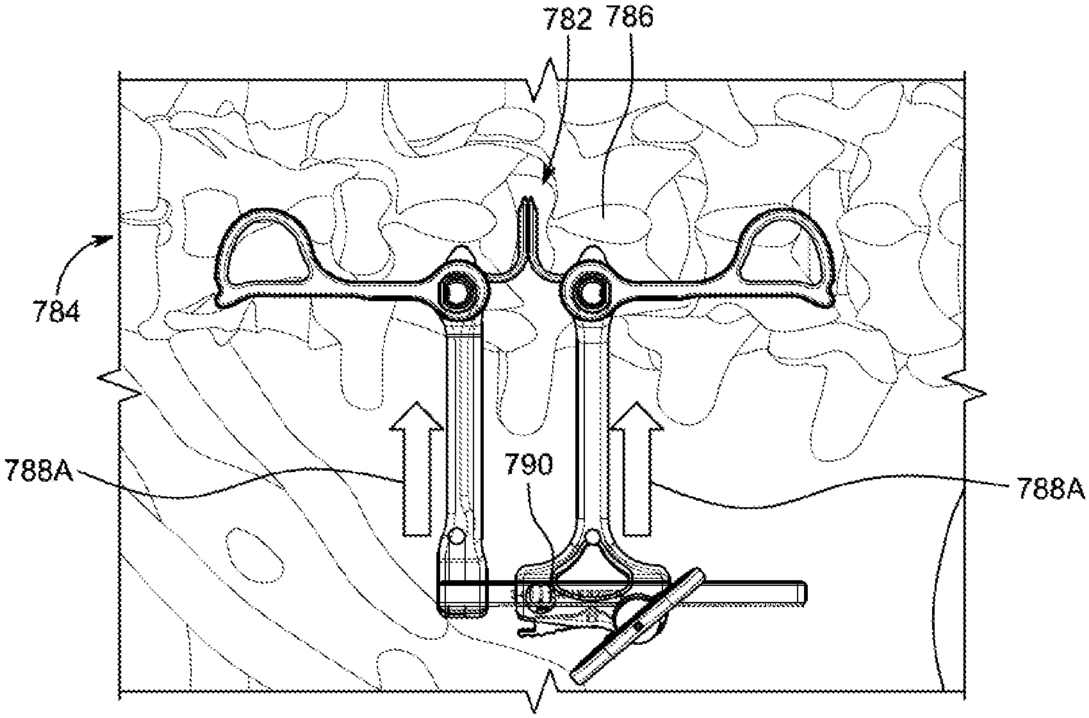
FIG. 7C4
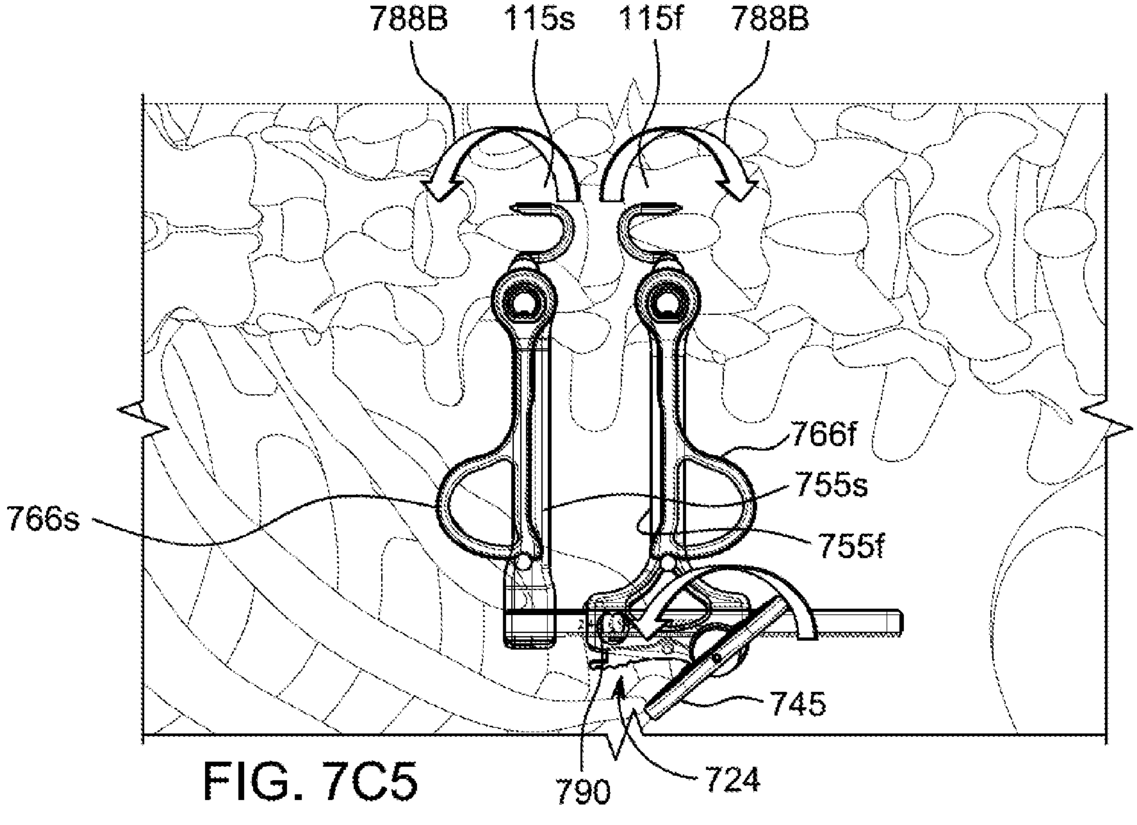
FIG. 7C5

SPINAL RETRACTOR BLADE AND RELATED RETRACTOR DEVICE AND METHOD

I. BACKGROUND OF THE INVENTION

A. Field of Invention

The invention generally relates to the field of spinal retractors.

B. Description of the Related Art

Surgical retractors have been known in various forms for many years. Naturally, there is no one retractor that is suitable for every procedure or every patient. Generally, retractors are designed to retract specific kinds of tissue or organs so as to expose a surgical field that is suitable for a specific procedure. More specifically, various specialized retractor blades are known for retracting specific kinds of tissue. For example, a retractor specifically adapted to retract skin is not necessarily well adapted to retract vertebrae. In certain procedures such as non-fusion decompression laminectomy interlaminar stabilization and Transforaminal Lumbar Interbody Fusion (TLIF) it is necessary to precisely size the gap between adjacent vertebrae to provide room for inserting a stabilizing device. Known retractors are not suitable for engaging the vertebrae e.g., utilizing the spinous processes. Spinal instrumentation manufacturers, including international manufacturers, of such non-fusion and fusion stabilizing devices do not provide spacing tools or retraction devices. The problem with these devices is that the vertebrae tend to move when the spacer and/or surgical retractors currently utilized are removed. Thus, the surgeon must repeatedly make adjustments of current retractors. Current retractors also damage or destroy tissue or slip of during use. This lengthens the procedure and increases anesthesia time as well as the chances that the patient may experience a complication like a dural leak, dural tear, nerve root injury, or infection. What is missing in the field is a retractor that is specifically designed for reliably engaging the vertebrae, spreading them to a predetermined degree, and holding them in position prior to inserting the stabilizing implant. Some embodiments of the present invention may provide one or more benefits or advantages over the prior art.

II. SUMMARY OF THE INVENTION

Some embodiments may relate to a retractor blade, comprising: a straight first leg having an end joined to an end of a shank, wherein the straight first leg is from zero cm to 6.0 cm in length; a straight second leg having a free end, the straight second leg oriented between 0° and 90° relative to the straight first leg, wherein the straight second leg is from zero cm to 6.0 cm in length; and a transition from the straight first leg to the straight second leg, wherein a minimum width ($w_{min}$) between the straight first leg and the straight second leg is operable to receive a spinous process.

Embodiments may relate to a spinal retractor, comprising: a first blade comprising: a straight first leg having an end joined to an end of a first shank; a straight second leg having a free end, the straight second leg oriented between 0° and 90° relative to the straight first leg; and a transition from the straight first leg to the straight second leg, wherein a minimum width ($w_{min}$) between the straight first leg and the straight second leg is operable to receive a spinous process; a second shank opposing the first shank; a shank spreader in spreadable communication with the first shank and the second shank; and a ratchet in ratcheting communication with the shank spreader.

Embodiments may further relate to a method of vertebral retraction comprising the steps of: providing a first vertebra and a second vertebra; providing a spinal retractor, comprising: a first blade comprising: a straight first leg having an end joined to an end of a first shank; a straight second leg having a free end, the straight second leg oriented between 0° and 90° relative to the straight first leg; and a transition from the straight first leg to the straight second leg, wherein a minimum width ($w_{min}$) between the straight first leg and the straight second leg is operable to receive a spinous process; a second shank opposing the first shank; a shank spreader in spreadable communication with the first shank and the second shank; and a ratchet in ratcheting communication with the shank spreader; orienting the straight second leg of the first blade and the straight second leg of the second blade parallel to each other; inserting the free end of the first blade and the free end of the second blade between the first vertebra and the second vertebra; piercing the interspinous ligament with the free end of the first blade and the free end of the second blade; rotating the first blade and the second blade around the first spinous process and the second spinous process so that the straight first leg of the first blade and the straight first leg of the second blade are parallel; actuating the shank spreader, causing the first blade to impinge a spinous process of the first vertebra; and separating the first vertebra from the second vertebra by a predetermined amount.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein:

FIG. 1 perspective view of a retractor blade embodiment incorporated in a retractor;

Figure 1:
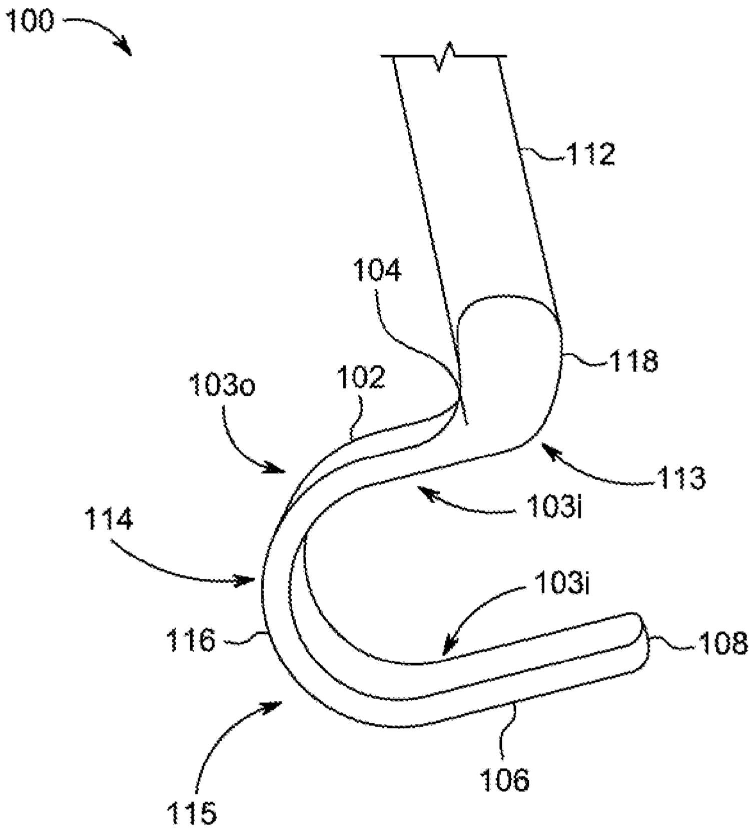
Figure 4:
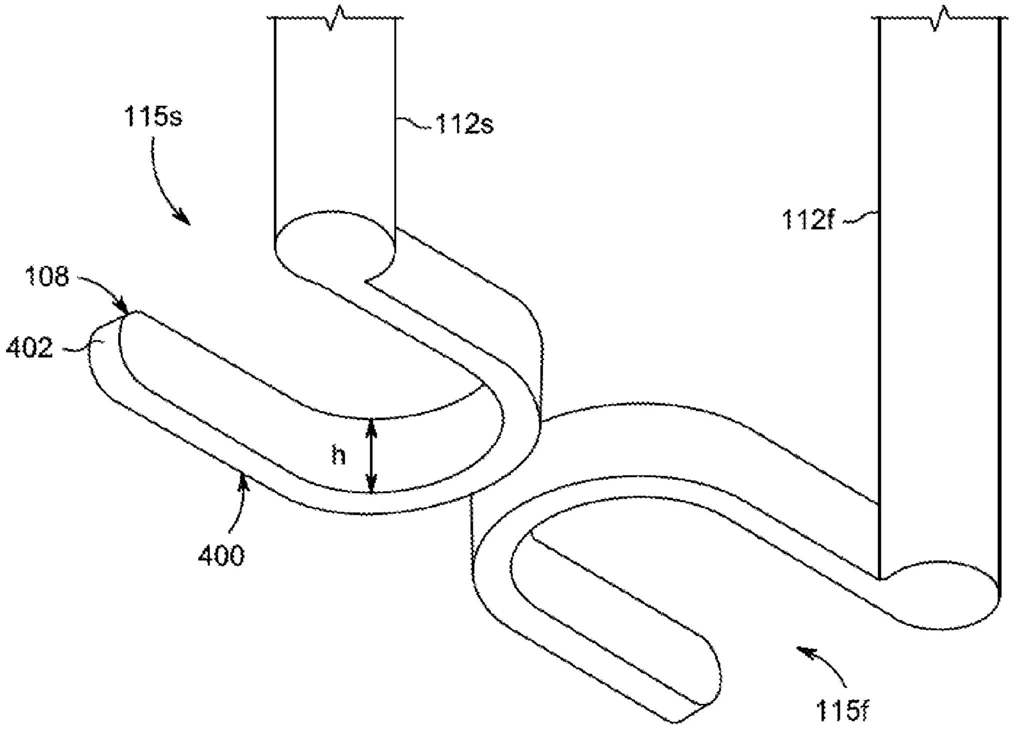
FIG. 4 is a partial view of a retractor embodiment having a pair of blades according to an embodiment of the invention.
Figure 5:
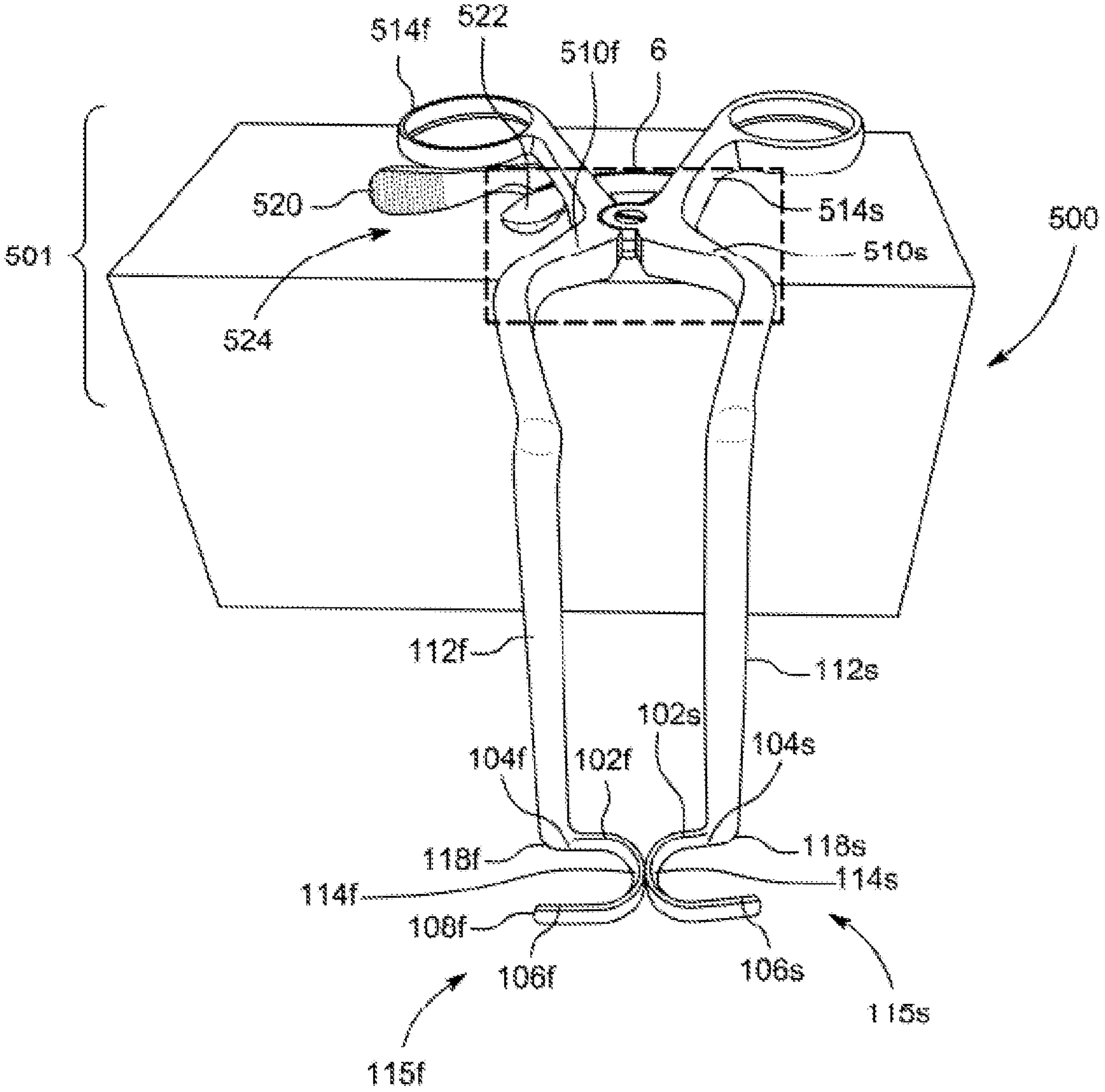
FIG. 5 is a front perspective view of a scissor-type retractor embodiment having a pair of blades according to an embodiment of the invention.
Figure 7A:
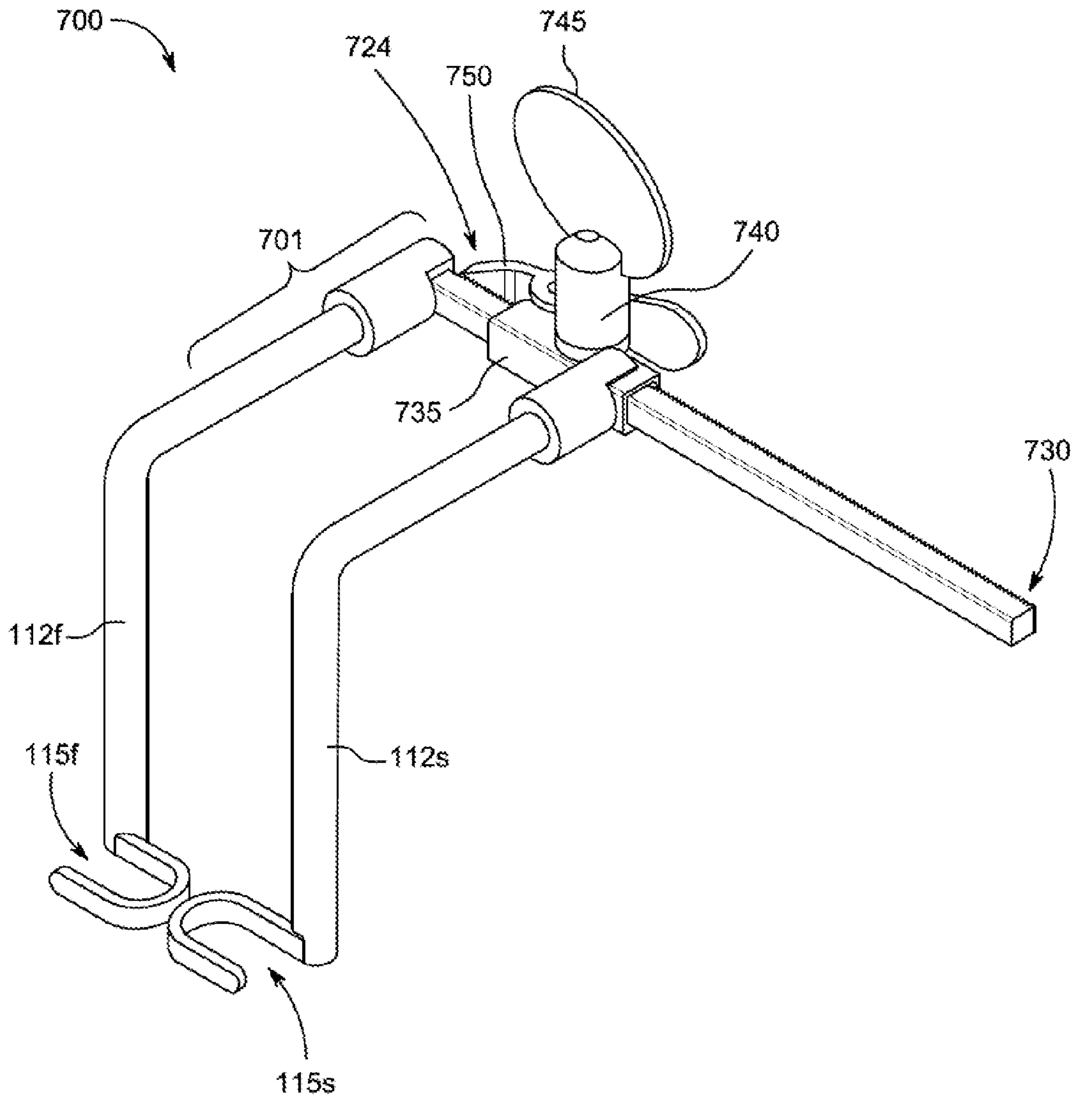
FIG. 7A is a front elevation view of a rack-and-pinion style retractor embodiment.
Figure 7B:
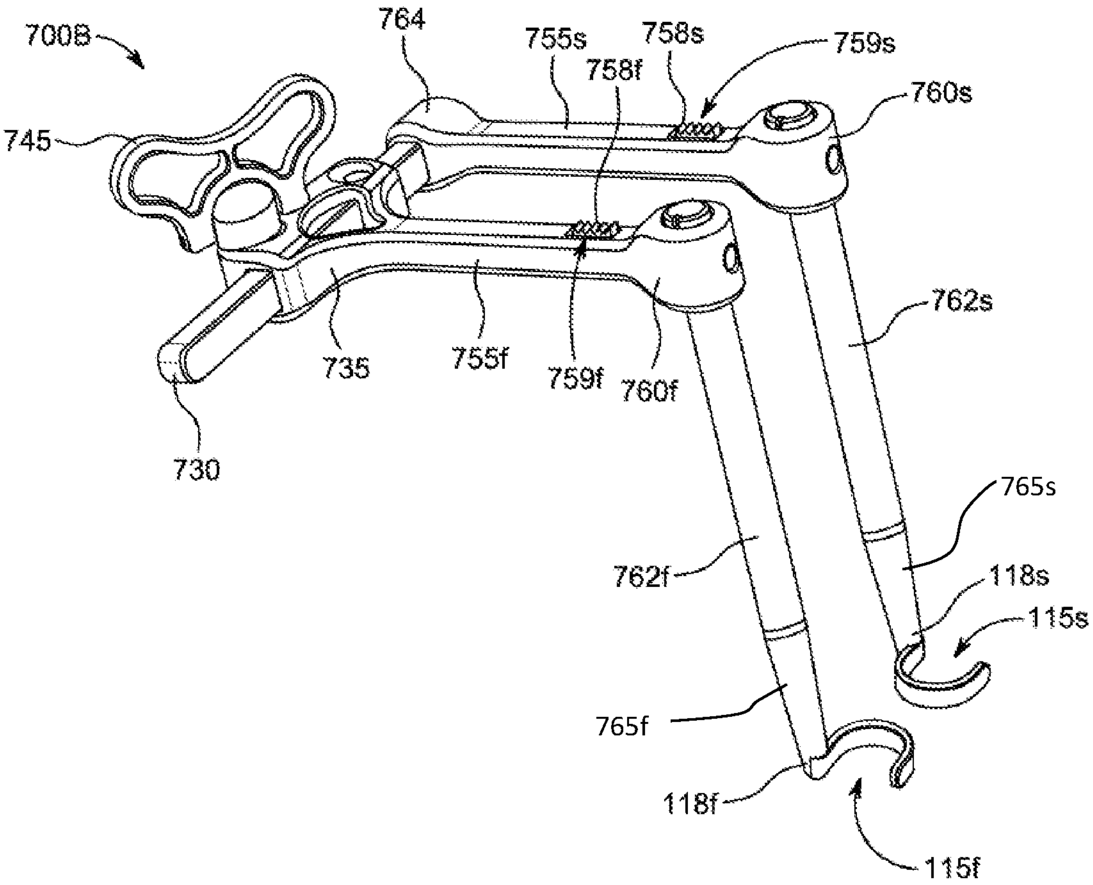
FIG. 7B is an elevation view of a rack-and-pinion style embodiment having releasable shanks.
Figure 7D:
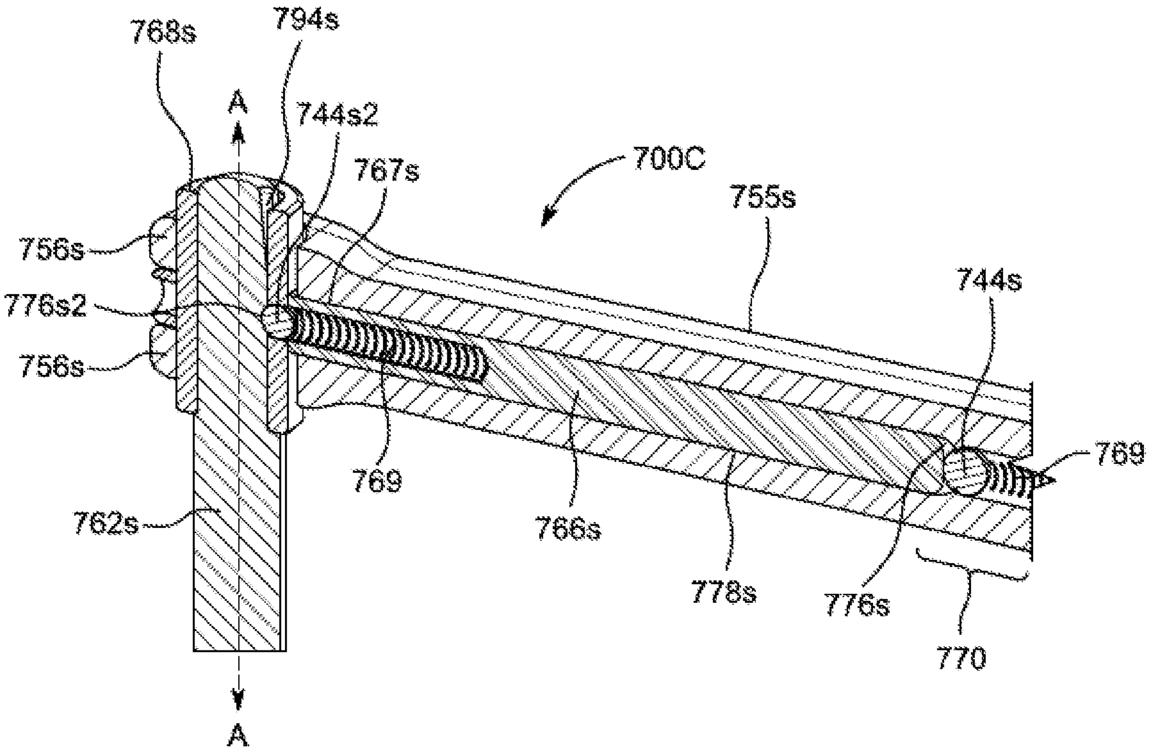
Figure 7E:
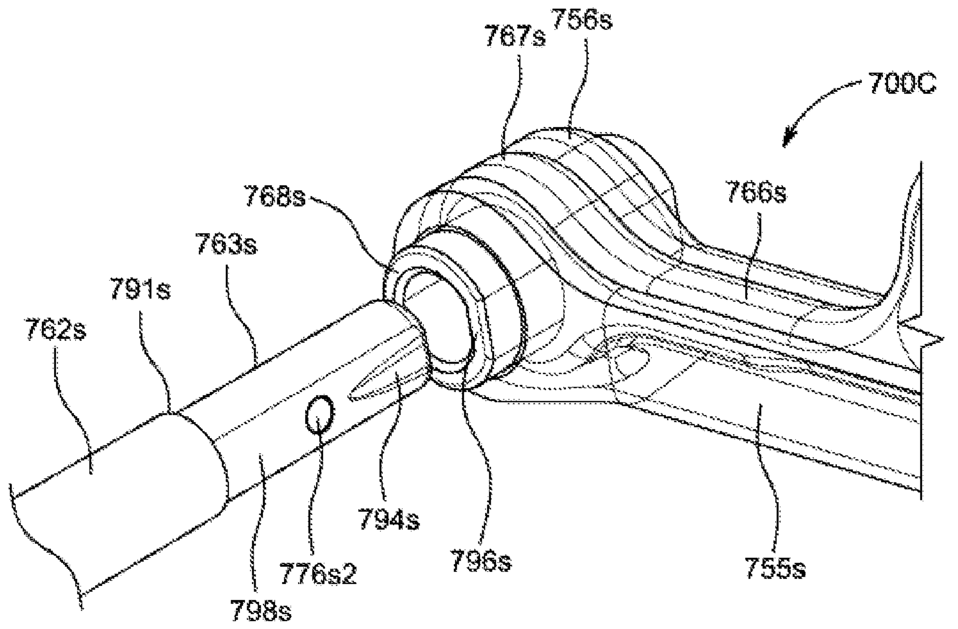
Figure 8:
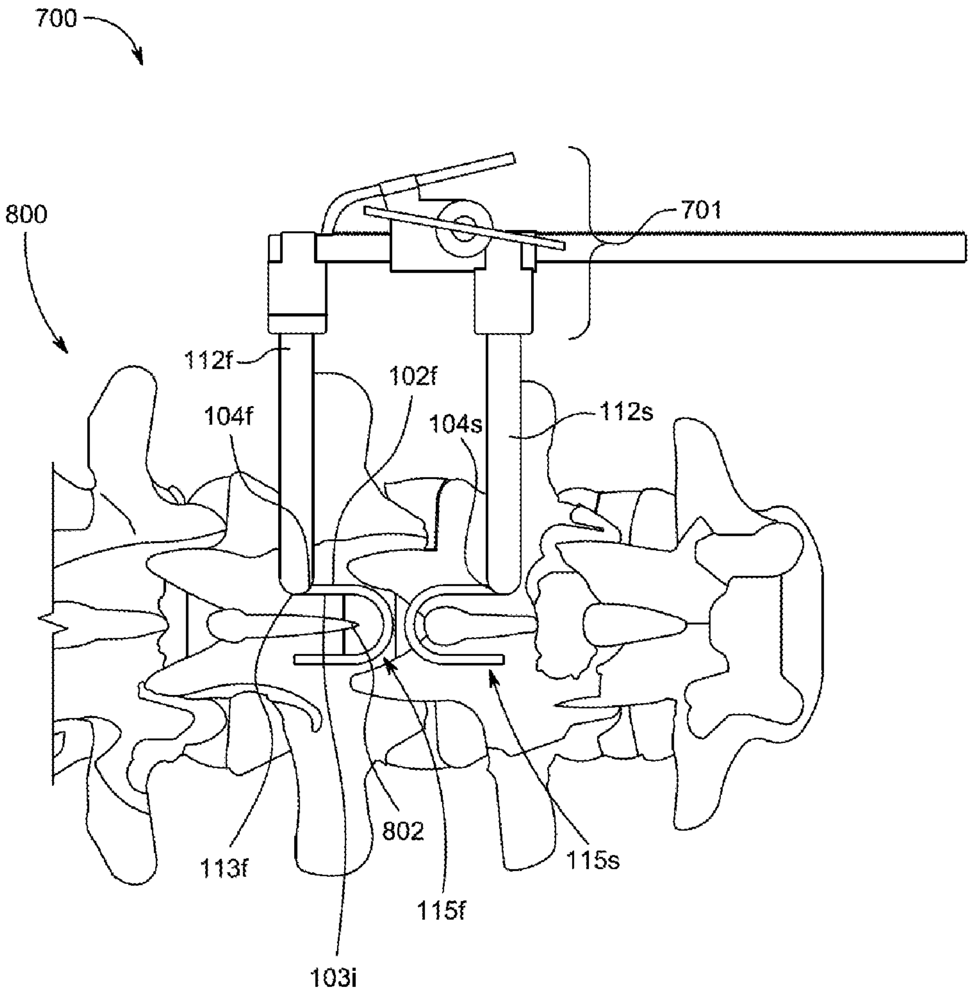
Figure 9:
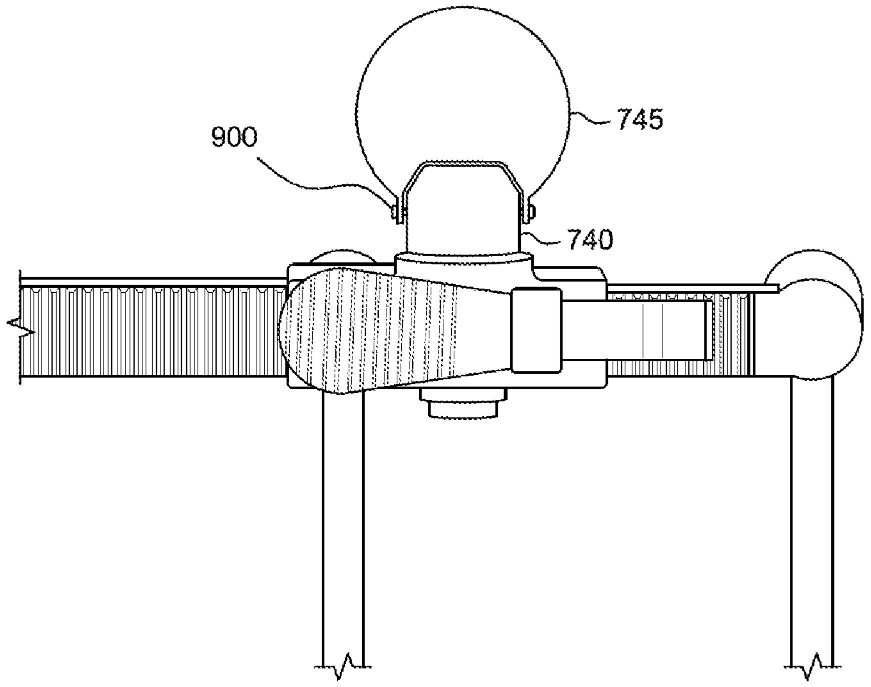
Figure 10:
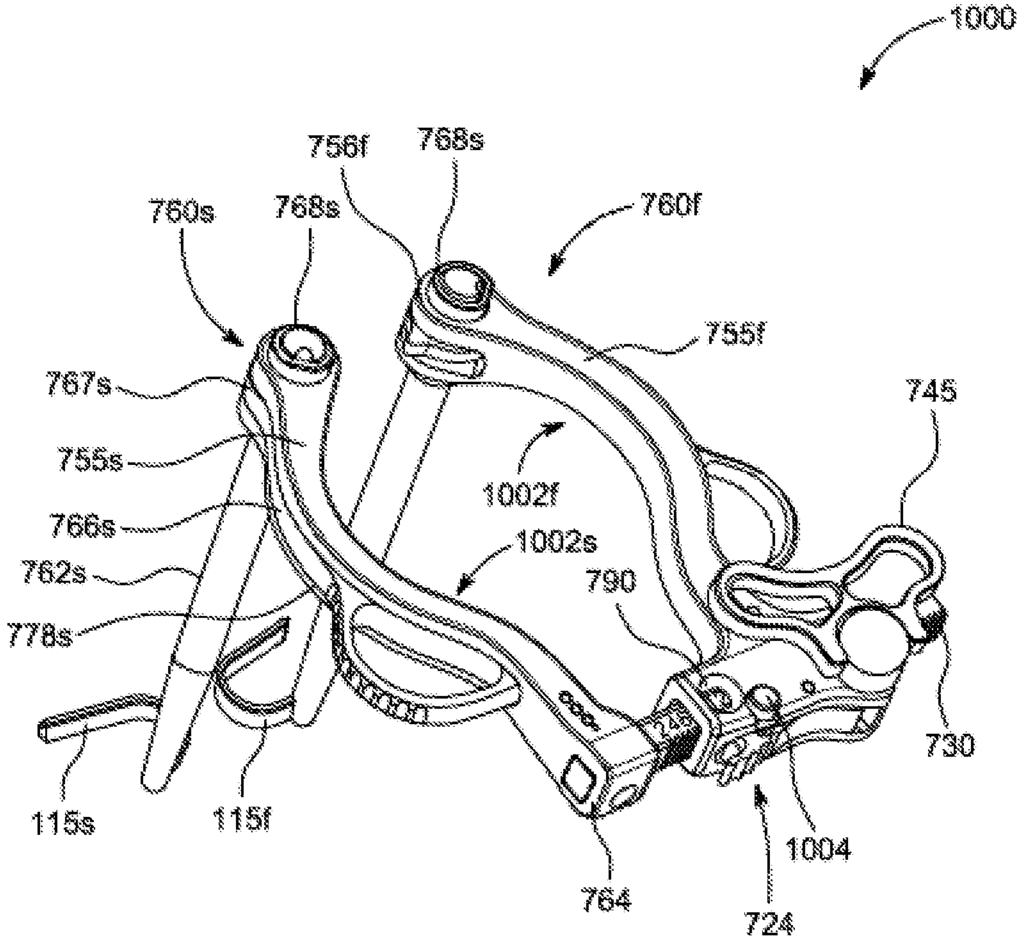
Figure 11:
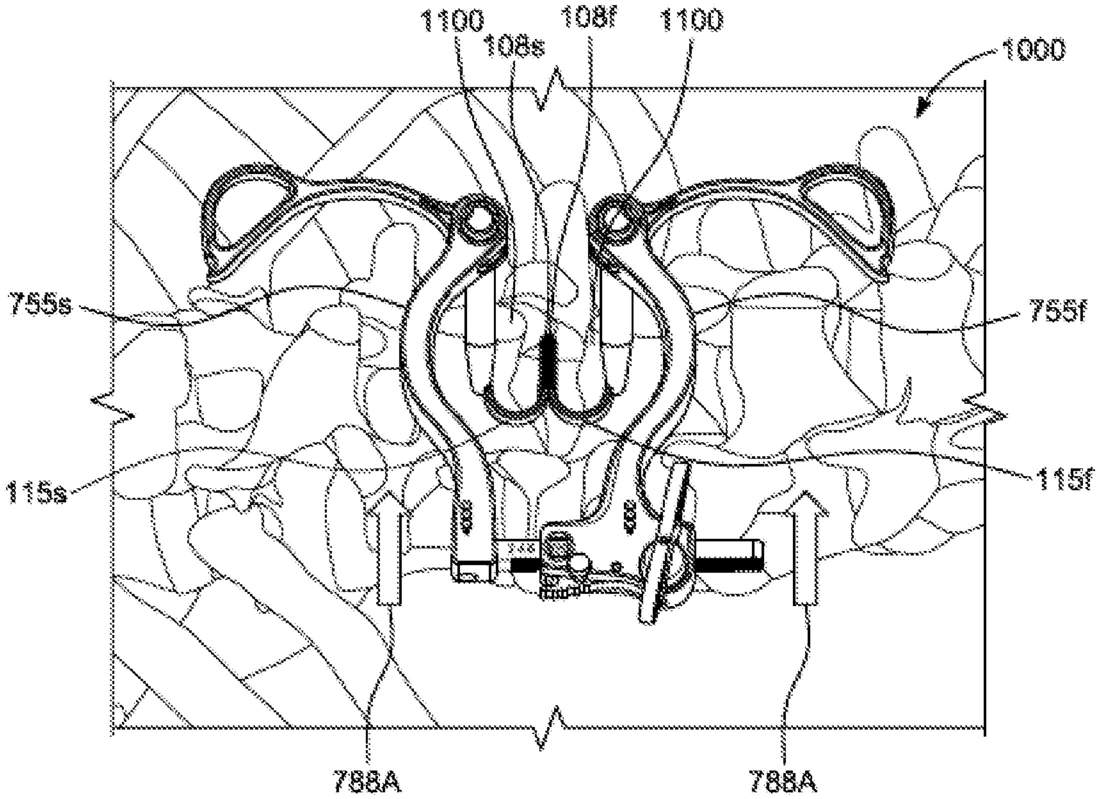
Figure 12:
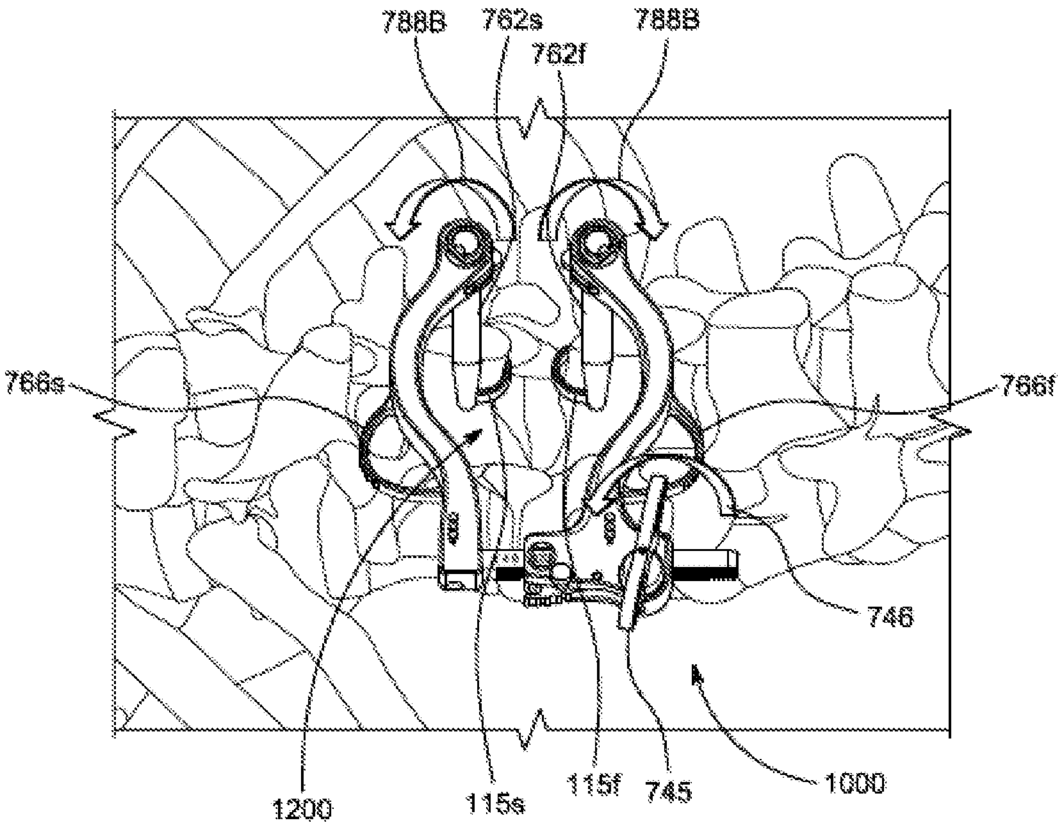
Figure 13:
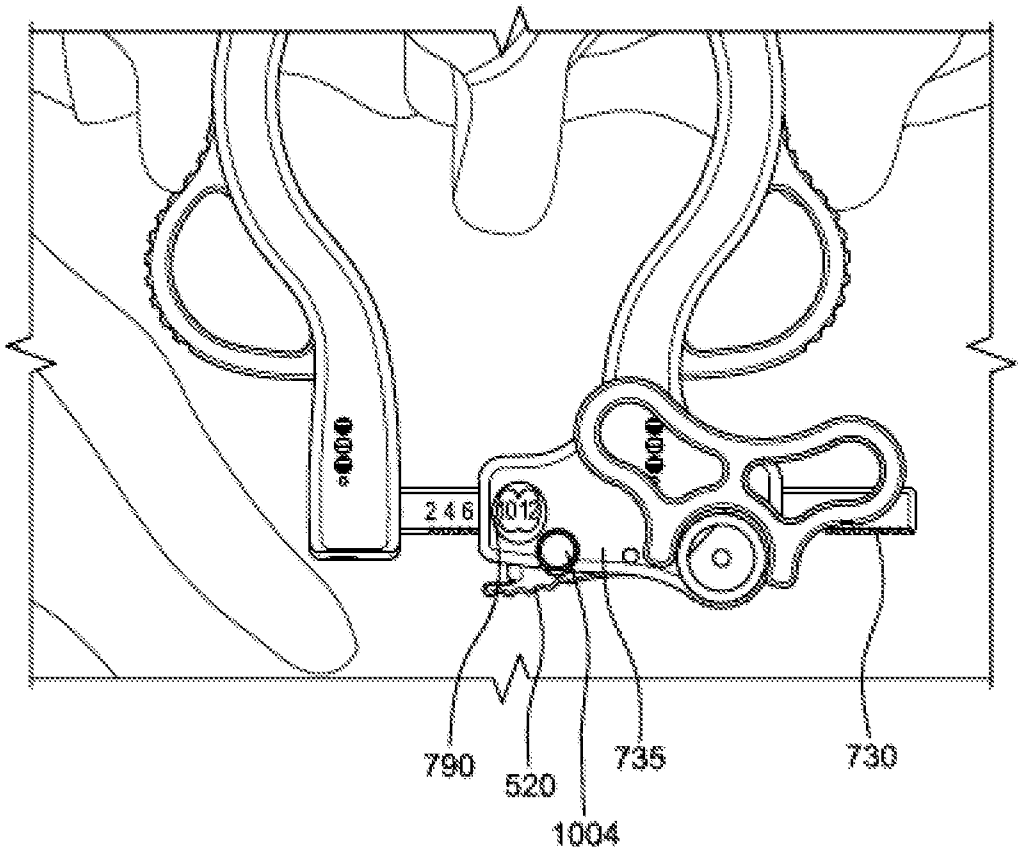
Figure 14:
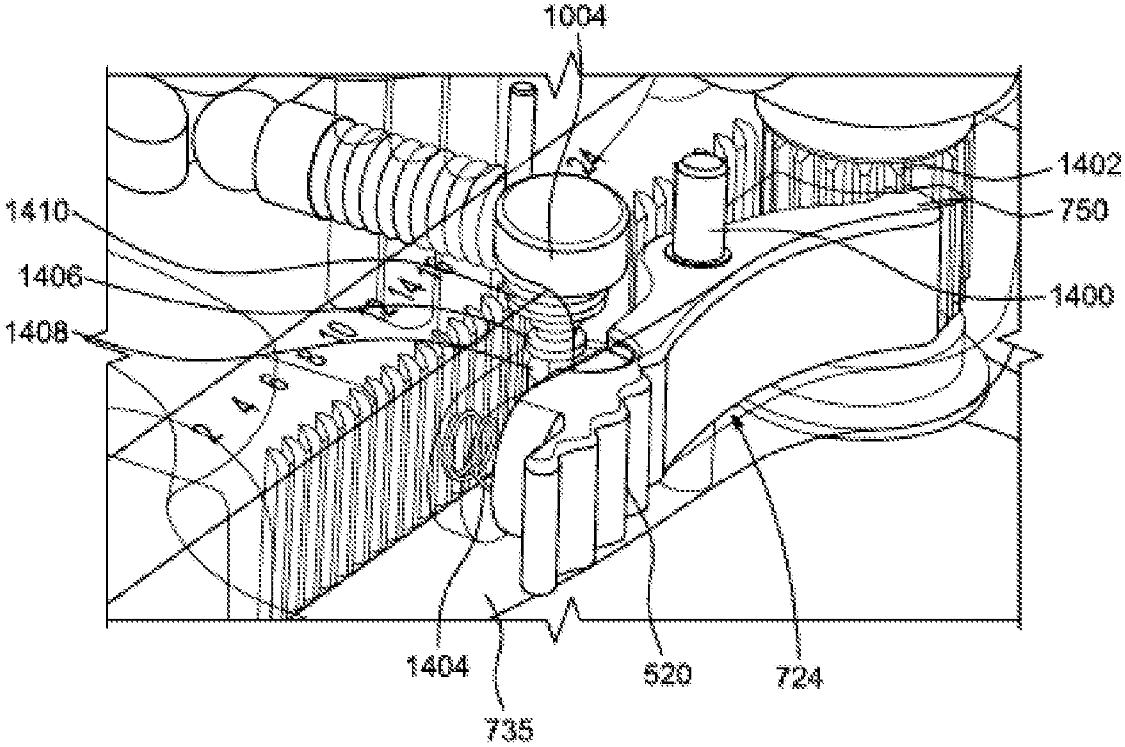
Figure 15A:
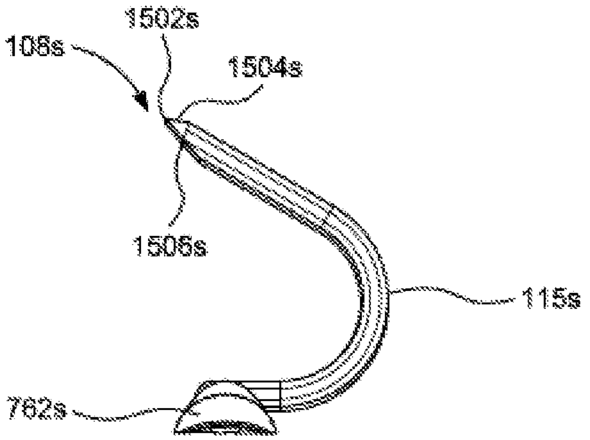
Figure 15B:
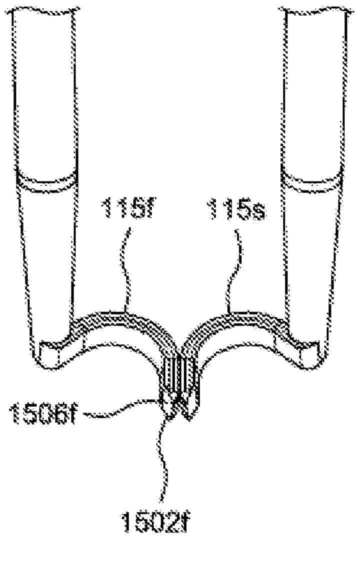

FIG. 7C1 is an elevation view of a rack-and-pinion embodiment having shanks that are releasable and rotatable;

FIG. 7C2 is a top view of the embodiment of FIG. 7C1 showing the blades in a closed configuration;

FIG. 7C3 is a top view of the embodiment of FIG. 7C1 showing the blades in an opened configuration;

FIG. 7C4 is a top view of the embodiment of FIG. 7C1 showing the blades in a closed configuration and in relation to a spinal column;

FIG. 7C5 is a top view of the embodiment of FIG. 7C1 showing the blades in an opened configuration and in relation to a spinal column;

FIG. 7D is a cross sectional view taken along line 7D-7D of the embodiment in FIG. 7C3;

FIG. 7E is a partial view of embodiment 700C illustrating the fit of the removable shank, and the mechanism for rotating the shank;

FIG. 8 is a downward view of a rack-and-pinion embodiment cooperating with a spine; and FIG. 9 is a perspective view of a rack and pinion embodiment having a folding handle;

FIG. 10 is an elevation view of an embodiment having arcuately shaped arms;

FIG. 11 is a top view of the embodiment shown in FIG. 10 illustrating insertion of the blades between two spinous processes;

FIG. 12 is a top view of the embodiment shown in FIG. 10 illustrating rotation of the blades around the spinous processes;

FIG. 13 is a close up view of the window indicator and ratchet latch;

FIG. 14 is a detail view showing the internal components of the ratchet and ratchet latch;

FIG. 15A is an illustration of a beveled free end of a retractor blade;

FIG. 15B is a front view of a pair of blades having beveled free ends; and

Figure 15C:
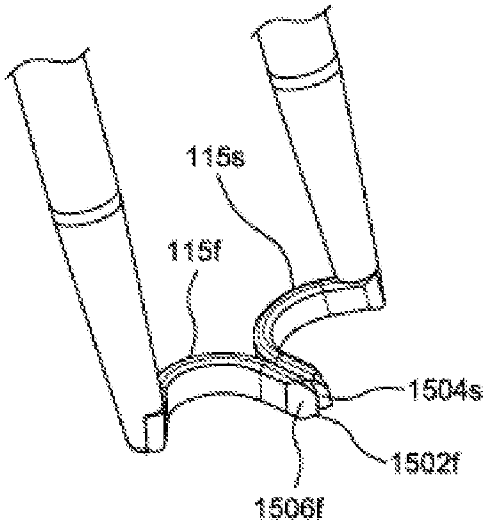

FIG. 15C is an oblique view of a pair of blades having beveled free ends.

IV. DETAILED DESCRIPTION OF THE INVENTION

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not require every element of a list or only one element of a list to the exclusion of others.

Terms of degree, terms of approximation, and/or subjective terms may be used herein to describe certain features or elements of the invention. In each case sufficient disclosure is provided to inform the person having ordinary skill in the art in accordance with the written description requirement and the definiteness requirement of 35 U.S.C. 112.

Referring now to the drawings wherein the showings are for purposes of illustrating embodiments of the invention only and not for purposes of limiting the same, FIG. 1 illustrates a retractor blade 115 embodiment 100. As described in more detail herein, retractor blades are often, but not necessarily, incorporated into spinal retractor embodiments in pairs. Thus, while the embodiment of FIG. 1 is described simply as a "retractor blade 115", the very same structure is referred to elsewhere herein as a "first retractor blade 115*f*". Though the structure is the same, the appended letter "f" is used to distinguish it from a "second retractor blade 115*s*".

With continuing reference to FIG. 1, the retractor blade 115 includes an optional straight first leg 102 having an end 104 that is joined to the end 118 of a shank 112 of a retractor. The rest of the retractor is out of view. In the illustrated embodiment 100 the end 104 of the retractor blade 115 is joined to the shank 112 through a welding process; however, in this context the word joined is intended to include any known means for connecting the blade 115 to the shank 112 of a retractor. For example, and without limitation, the word joined includes the blade and shank being cast from a common mold, the blade and shank being formed from a common rod e.g., by bending the rod to a desired shape, welding, or the blade being fastened to the shank as with a rivet or other known fastener.

Regardless of how the blade 115 is joined to the shank 112, it is desirable, though not required, to position the shank 112 on an outside face 103*o* of the blade 115. Thus, a face 113 of an end 118 of the shank 112 may be joined to the end 104 of the blade. Equivalently, a face 113 of an end 118 of the shank 112 may be joined to an outside face 103*o* of the blade 115 near the end 104.

FIG. 1 also shows an optional straight second leg 106 connected to the optional straight first leg 102 through a transition 114. The transition 114 may be arcuate, as shown, and thus may have an apex 116. The specific morphology of the illustrated transition 114 is a circular arc; however, the person having ordinary skill in the art will readily understand that the invention is not limited to circular arcs or arcuate morphologies in general. It will be understood by the ordinarily skilled artisan that the legs 102, 106 comprise the straight portions of the blade 115, as shown in FIG. 1, and the transition 114 comprises the balance of the blade 115. The straight second leg 106 terminates in a free end 108, and the straight second leg 106 is oriented parallel the straight first leg 102. The free end 108 illustrated here is rounded; however, the invention is not limited to rounded free ends 108. Other morphologies, including a bevel, are illustrated elsewhere herein.

Figure 2A:
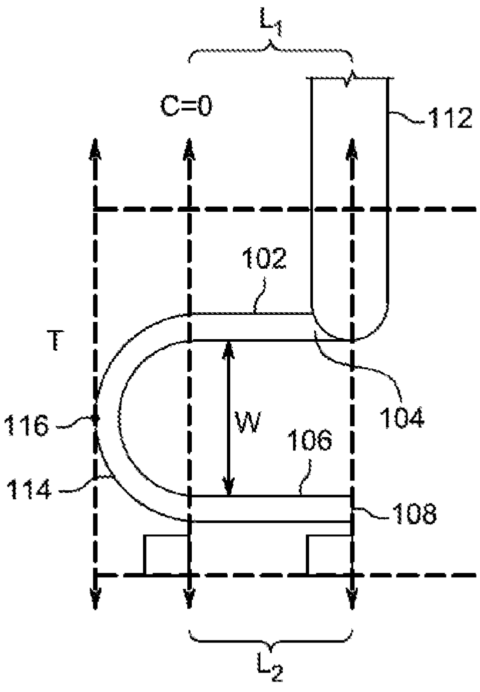
FIG. 2A is a top view of an embodiment having a straight second leg terminating along a center line of a shank.

FIG. 2A a top view of a blade embodiment where the spacing between the straight first leg 102 and the straight second leg 106 is indicated by letter "w". The spacing w can vary substantially from one embodiment to another because an operable spacing depends on the size of the spinous process with which it is to cooperate. Spinous processes vary in size from one patient to another, and from one vertebra to another within the same patient. The person having ordinary skill in the art will understand that the fit between the blade 115 and spinous process is not critical. Thus, a given blade size may be operable in connection with varying sizes of spinous processes; however, the governing principle is that the blade must be large enough to receive the spinous process yet small enough to fit between two adjacent spinous processes without unduly interfering with the surgeon's view or surrounding tissues. This principle provides parameters within which the person having ordinary skill in the art can determine operable dimensions without undue experimentation. However, operable dimensional ranges include a width w from about 0.3 cm to 2.0 cm+/−10%; the length ($L_1$, $L_2$) of a straight first leg 102 or straight second leg 106 may be from zero to 6.0 cm+/−10%; and, the height h of the blade as described in more detail subsequently herein may be from about 0.3 cm to 4.0 cm+/−10%.

Figure 2B:
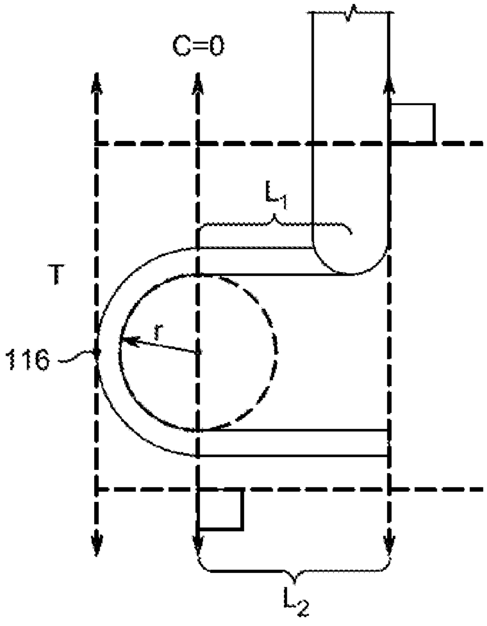
FIG. 2B is a top view of an embodiment having a straight second leg somewhat longer than that of FIG. 2A.
Figure 2C:
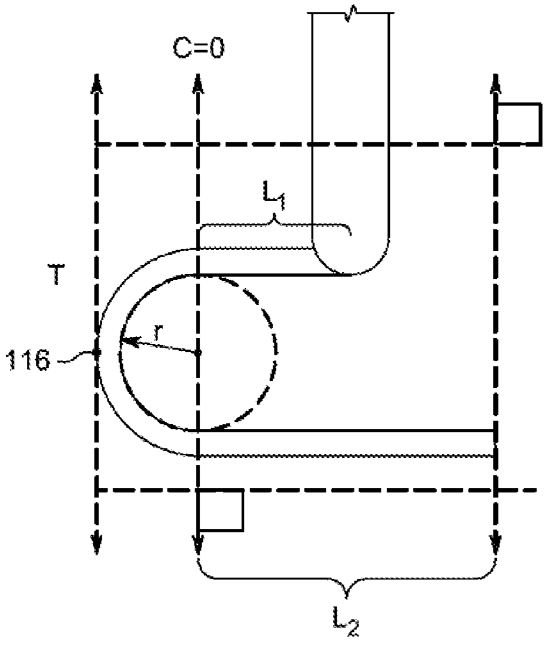
FIG. 2C is a top view of an embodiment having a straight second leg somewhat longer than that of FIG. 2B.

With continuing reference to FIG. 2A, the length of the straight first leg 102 is denoted $L_1$. $L_1$ is measured from an end (line C=0) of the transition 114 to the end 104 of the region where the straight first leg 102 is joined to shank 112. Similarly, the length of the straight second leg 106 is denoted by $L_2$. $L_2$ is measured from an end (line C=0) of transition 114 to the free end 108 of the straight second leg 106. The ends of the transition 114 are indicated by the line C=0 which is the point at which the curvature of the blade becomes zero. Stated equivalently, the length $L_2$ of the straight second leg 106 is determined by the length of the blade exceeding the distance between a tangent line T of an apex 116 of the transition 114 and a parallel line drawn through an end of the straight second leg 106 most proximal to the tangent line T. As shown in FIGS. 2B and 2C, the straight second leg 106 can extend an arbitrary distance beyond the centerline of the shank 112, constrained only by the requirement that the blade must fit between two spinous processes without unduly interfering with the surgeon's view or surrounding tissues. FIGS. 2B and 2C also illustrate that the embodiment shown therein comprises a circular arc transition having a radius r and an apex 116 at 90° between the first and second straight legs 102, 106. Further, the transition 114 can be defined as the region of the blade falling between line C=0 and the tangent line T through apex 116, where lines C=0 and T are parallel to each other.

The lengths $L_1$, $L_2$ of the straight first and second legs 102, 106 can vary from one embodiment to another according to the anatomy of the patient; however, the upper limit of the lengths is constrained by the legs' interference with adjacent tissues and vertebrae. In other words, if the legs 102, 106 are too long they will impinge upon adjacent vertebrae and potentially cause tissue damage or interfere with the fit or use of the device. There is no lower limit to the length of the legs 102, 106. The lengths $L_1$, $L_2$ may either or both be zero, thus leaving only the transition. However, it may be advantageous to include legs 102 and/or 106 to better stabilize the device and improve its grip of the spinous processes. Nonetheless, as described further in reference to FIGS. 3A-3D, embodiments are contemplated, and claimed herein, where straight first and/or second legs 102, 106 are absent.

Figure 3A:
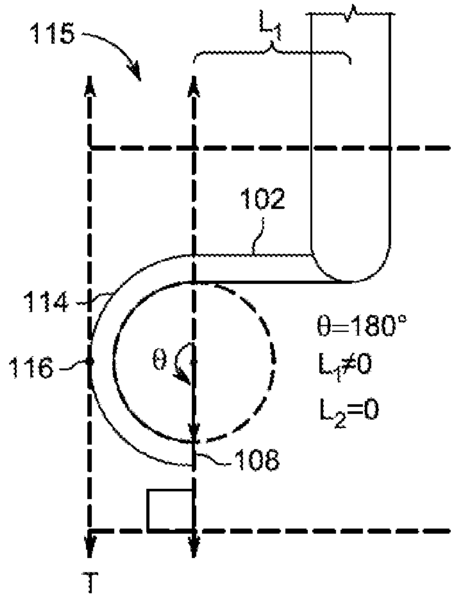
FIG. 3A is a top view of an embodiment having no straight second leg and having a 180° full transition.
Figure 3B:
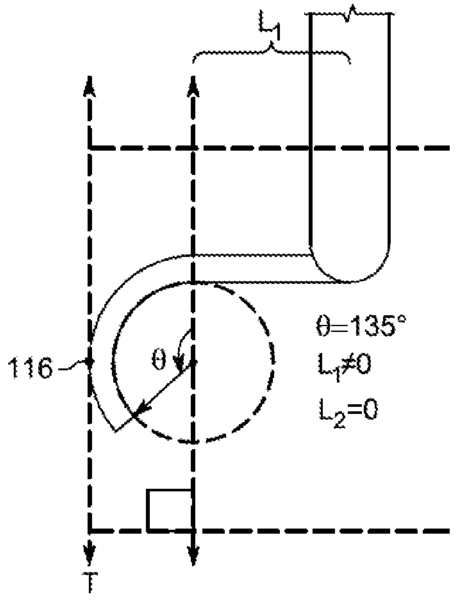
FIG. 3B is a top view of an embodiment having no straight second leg and having a 135° partial transition.
Figure 3C:
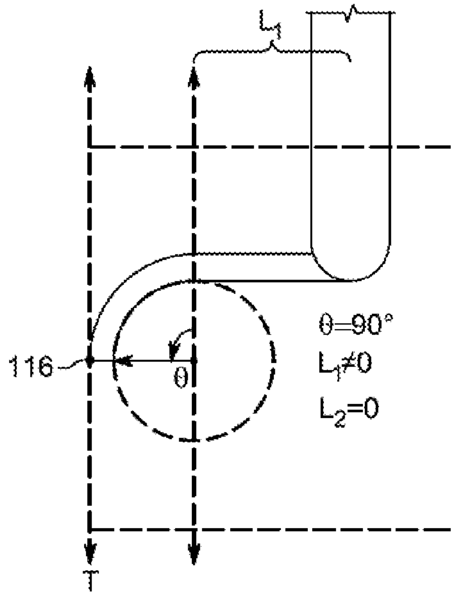
FIG. 3C is a top view of an embodiment having no straight second leg and having a 90° partial transition.
Figure 3D:
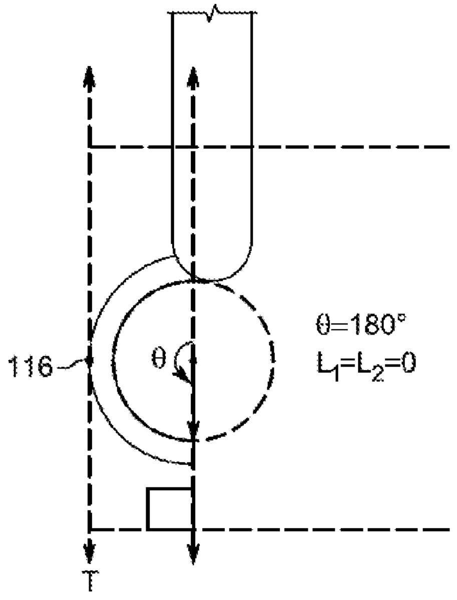
FIG. 3D is a top view of an embodiment having not straight first or second leg.
Figure 3E:
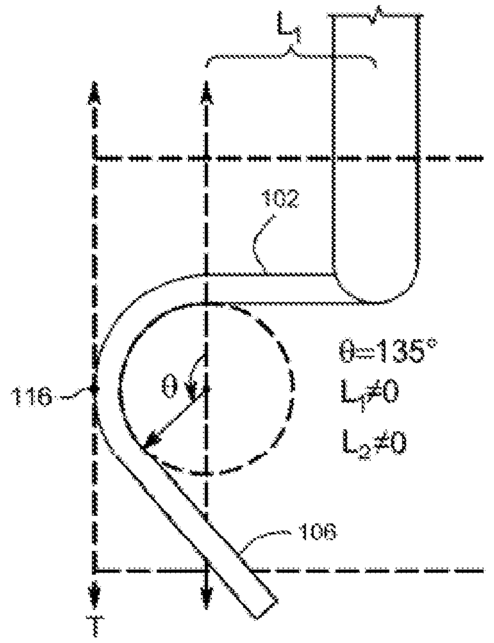
FIG. 3E is a top view of an embodiment having non-parallel first and second legs.
Figure 3F:
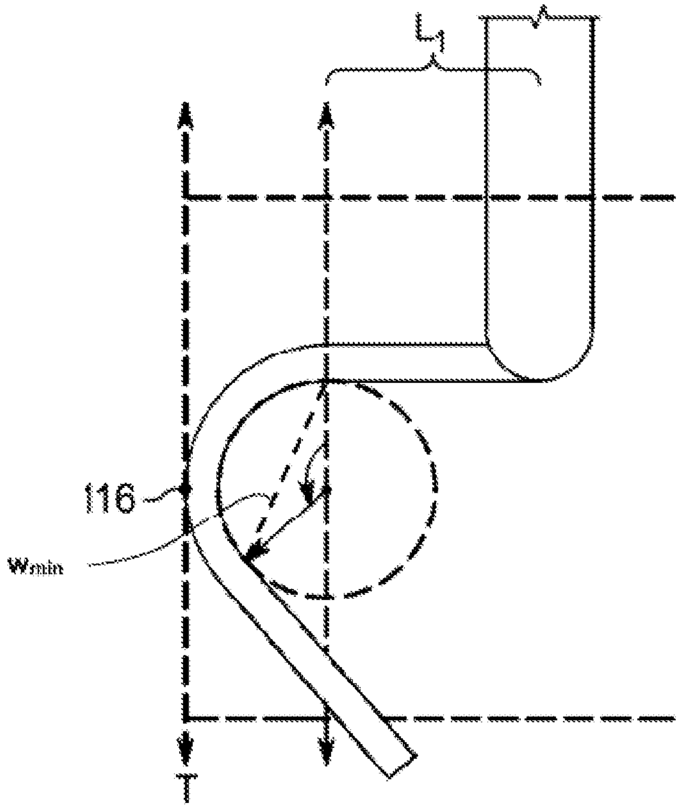
FIG. 3F is the embodiment illustrated in FIG. 3E but further illustrating the minimum width $W_{min}$.

FIGS. 3A through 3C illustrate embodiments lacking a straight second leg 106 ($L_2$=O), but having a straight first leg ($L_1 \neq 0$). Though the straight second leg 106 may be advantageous in certain embodiments, it is not a requirement. The necessary cooperation between a blade 115 according to the invention and a spinous process can be achieved with less material. For example, and without limitation, in FIG. 3A a θ=180° transition 114 is provided but the blade 115 terminates 108 without extending into a straight second leg. Similarly, in FIG. 3B a partial transition of θ=135° is provided, and in FIG. 3C a partial transition of θ=90° is provided. Again, these drawings are not intended to limit the invention to a particular morphologies or arc length(s) of transition 114. Rather, they are intended to illustrate that any length can be suitable, even a length of θ=90°, provided that the blade can separate vertebrae without sliding off the spinous processes. FIG. 3D illustrates an embodiment where both the straight first leg 102 and the straight second leg 106 are absent, that is where $L_1=L_2=0$. FIG. 3E illustrates an embodiment where a partial transition of θ=135° is provided and $L_1$ and $L_2$ are both non-zero, $L_1=L_2\neq 0$. According to the embodiment in FIG. 3E the straight second leg 106 is oriented at 45° to the straight first leg 102. Similar to the embodiments of FIGS. 3A-3D, where the straight first 102 and/or second leg 106 is/are absent ($L_2$=0), θ may have any value from 90° to 180°, 90°≤θ≤180° and the first straight leg 102 may be absent ($L_1$=θ). FIG. 3F shows the same embodiment as FIG. 3E with an annotation illustrating the minimum width $w_{min}$ between the straight first and second legs 102, 106. The minimum width $w_{min}$ is defined as the distance from the ends of the straight first and second legs 102, 106 that are most proximal to apex 116. The ends correspond to the point where the curvature of the transition 114 becomes zero. This width is referred to as the minimum because the distance between the straight first and second legs 102, 106 increases with increasing distance from the apex 116. The minimum width $w_{min}$ of any given embodiment is operable to receive a spinous process.

Table I shows dimensions of spinous processes of male and female L1 to L5 vertebrae.

| Spinous Process | Size Range (mm) | Mean Size (mm) Male | Female | SD |
|---|---|---|---|---|
| | | Height | | |
| L1 | 16-36 | 26 | 23 | 4 |
| L2 | 18-35 | 27 | 24 | 3 |
| L3 | 18-38 | 27 | 24 | 3 |
| L4 | 14-32 | 24 | 21 | 3 |
| L5 | 10-34 | 20 | 18 | 4 |
| | | Width | | |
| L1 | 6-16 | 11 | 10 | 2 |
| L2 | 6-16 | 11 | 10 | 2 |
| L3 | 5-17 | 11 | 10 | 2 |
| L4 | 4-18 | 9 | 8 | 2 |
| L5 | 3-15 | 9 | 8 | 2 |

Turning to FIG. 4, a pair of opposing blades **115*f*, 115*s* joined to opposing shanks 112*f*, 112*s* is shown. The blades 115*f*, 115*s* comprise a flat band 400 of material having arcuate free ends 108 defining apexes 402. The shape of the free end may advantageously, but not necessarily, be arcuate. Other advantageous morphologies include beveled free ends, as will be described in more detail herein. An advantage to an arcuate end 108 is that it tends to prevent or limit damage to surrounding tissues. The height h of the band 400** is not critical; however, it must cooperate with a spinous process. Thus, its height h is constrained by the blade's ability to fit between adjacent spinous processes without unduly interfering with or damaging the surrounding tissue. For example, the person having ordinary skill in the art will understand that a certain amount of force must be applied to adjacent spinous processes to separate them. Thus, a blade having an excessively small height h would apply too much force to a small area, unnecessarily cutting into the tissue. At the other extreme, an excessively large height h would add more material to the blades without adding more contact area with the spinous processes. The foregoing explanation provides parameters within which the person having ordinary skill in the art can determine operable dimensions without undue experimentation.

As discussed above with reference to FIG. 4, the free end 108 of a blade (115*f* and/or 115*s*) may be arcuate and may define a smooth apex 402, which may prevent damage to surrounding tissue. However, alternative morphologies may also be beneficial. For example, the free end 108 may have a beveled edge as shown in FIGS. 15A-15C. FIG. 15A illustrates a second blade 115*s* attached to a vertical shank 762*s* in isolation. As used herein, the term "vertical shank" does not limit the invention to a particular orientation. Rather, "vertical shank" merely means that the shank is straight, rather than angled in the nature of structures 112*f* and 112*s*. The free end 108 comprises a sharpened apex 1502*s* formed by a first planar surface 1504*s* and a second planar surface 1506*s*. FIGS. 15B and 15C illustrate the same second blade 115*s* in context of a first blade 115*f* from a front elevation view 15B and a side elevation view 15C. Similar to the second blade 115*s*, the first blade 115*f* comprises a first planar surface 1504*f* and a second planar surface 1506*s* that together form a sharpened apex 1502*f*. One benefit conferred by a beveled free end 108 is that it can cut through interspinous ligament tissue that obstructs the retractor embodiment in a side-loading procedure, described elsewhere herein. The invention is not limited to beveled free ends having planar surfaces. Rather, one or more of the surfaces comprising a bevel may be curved.

Figure 6:
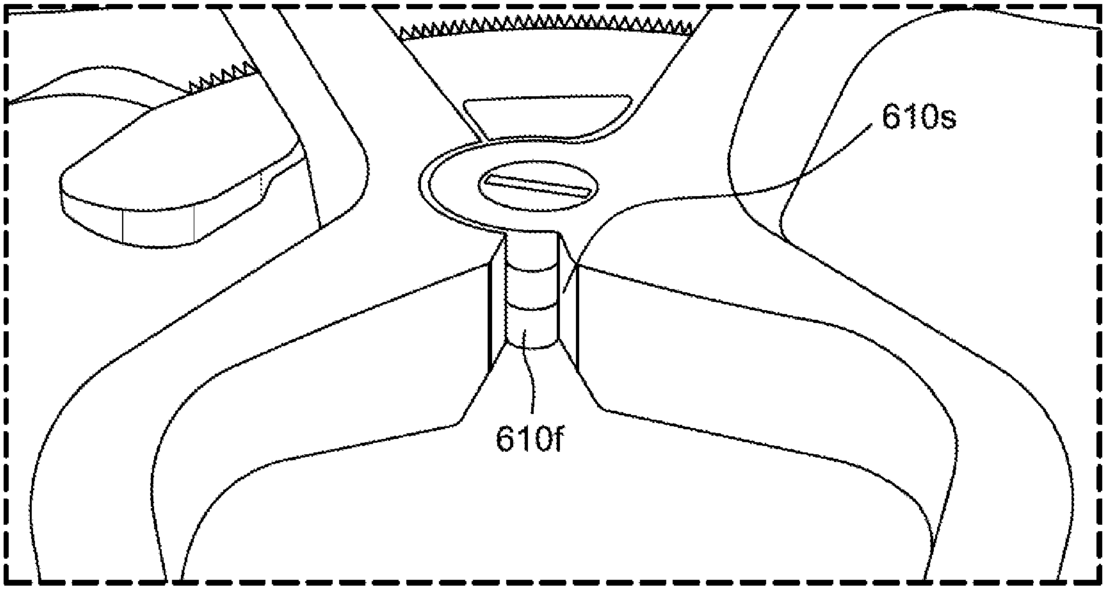
FIG. 6 is a magnified partial view of the portion of FIG. 5 enclosed in box 6.

FIG. 5 is a front elevation view of a scissor-style embodiment 500. The shank spreader 501 has a first member 510*f* and a second member 510*s*. The first member 510*f* has a first handle 514*f* and a first shank 112*f*. Similarly, the second member 510*s* has a second handle 514*s* and a second shank 112*s*. The shank spreader 501 further includes the structure contained in box 6 of FIG. 5. This structure can be seen in greater detail in FIG. 6, which is a magnified partial view of the embodiment 500 in FIG. 5. The first and second members 510*f*, 510*s* are shown pivotably joined through the first pivot joint 610*f* and the second pivot joint 610*s* according to any suitable known means.

With continuing reference to FIG. 5, the shank spreader 501 further includes a ratchet 524 comprising an arcuate gear strip 522 and a spring-loaded pawl handle 520. The pawl handle 520 is biased toward the gear strip 522, therefore, the ratchet is disengaged by pulling back on the pawl handle 520. According to the embodiment 500 of FIG. 5, the retractor includes shanks 112*f*, 112*s* having a 90° bend, which prevents the surgeon's hands from obstructing his view of the surgical field. The 90° bend is an advantageous feature but not a requirement of the invention. A first blade 115*f* is disposed at an end 118*f* of the first shank 112*f*. Similarly, a second blade 115*s* is disposed at an end 118*s* of the first shank 112*s*. The blades 115*f*, 115*s* are the same structure previously described in reference to FIG. 1. Accordingly, both have an optional straight first leg 102*f*, 102*s*; a transition 114*f*, 114*fs*; an optional straight second leg 106*f*, 106*s*; an end 104*f*, 104*s* joined to the end 118*f*, 118*s* of opposing shanks 112*f*, 112*s*; and a free end 108*f*, 108*s*.

FIG. 7A is an illustration of a rack-and-pinion style retractor embodiment 700. The shank spreader 701 of this embodiment comprises a rack 730 fixedly joined according to any suitable known means to a first shank 112*f*. As used herein the term fixedly joined does not limit the invention to particular design choices, but rather is intended to be broadly construed to include any structure or structures that fix the orientation of one member to another, even including unitary parts made from a common mold. The gear teeth of the rack 730 are facing into the page out of view. The shank spreader 701 further includes a carrier 735 fixedly joined to the second shank 112*s* that slidably engages the rack. The carrier 735 includes a knob 740 and handle 745 that rotatably communicates with a pinion gear contained within the carrier 735 and out of view. The pinion gear engages the teeth of the rack 730. Therefore, turning the knob 740 clockwise moves the carrier 735 linearly along the rack 730, thereby spreading the blades 115*f*, 115*s* apart. This is also referred to herein as the carrier slidably engaging the rack through the pinion gear. The carrier also includes a ratchet 724 mounted thereto. The ratchet 724 includes a pawl 750, which engages the teeth of the rack 730 such that it allows the carrier 735 to spread the blades 115*f*, 115*s* but must be disengaged to bring the blades back together. The cooperative action of the components of the shank spreader 701 resulting in the blades 115*f*, 115*s* being spread apart or brought back together, is referred to herein as spreadable communication. In the embodiments shown in FIGS. 7B-7E and 10-14, which have vertical shanks 762*f*, 762*s*, the shank spreader 701 also comprises the arms 755*f*, 755*s*. In contrast, in the embodiment shown in FIG. 7A, the first shank 112*f* is part of the carrier 735 and the second shank 112*s* is directly joined to the rack 730, whereas embodiments having vertical shanks also have arms 755*f*, 755*s* interposed between the carrier 735 and the rack 730.

FIG. 7B illustrates a second rack-and-pinion style embodiment 700B. Embodiment 700B differs from embodiment 700 in that the carrier 735 includes an integrated first arm 755*f* terminating in a first socket 760*f* at one end. The first socket 760*f* includes a release mechanism 759*f* configured to receive and releasably engage a vertical shank 762*f*. Embodiment 700B thus substitutes the shanks 112*f*, 112*s* of embodiment 700 having a 90° bend with straight shanks 762*f*, 762*s*. The release mechanism 759*f*, 759*s* can comprise a variety of structures well known to persons having ordinary skill in the art, and the present invention is thus not limited to the particular mechanical arrangements specifically discussed herein. However, by way of example, in embodiment 700B the mechanism includes a slide 758*f*, 758*s* in spring-loaded communication with a locking pin (not shown). The pin is retained within the arm 755*f*, 755*s* and biased toward a recessed seat (not shown) in the shank 762*f*, 762*s*. Thus, when the locking pin engages the recessed seat, the shank 762*f*, 762*s* cannot be withdrawn unless the slide 758*f*, 758*s* is pulled back, disengaging the locking pin and releasing the shank 762*f*, 762*s*.

Similar to embodiment 700, embodiment 700B includes a second arm 755*s* that terminates at one end with a socket 764 connected, e.g. in an interference fit, with one end of the rack 730. Unlike embodiment 700 (FIG. 7A), the other end of the second arm 755*s* terminates in a second socket 760*s* that releasably engages with the second shank 762*s*. According to embodiment 700B shanks 762*f*, 762*s* may be changed out for shanks having alternative blade 115*f*, 115*s* sizes, θ angles, and/or morphologies. Thus, the user can have a single retractor that cooperates with a wide range of spinous process sizes.

Embodiment 700B of FIG. 7B also differs from embodiment 700 in that it includes tapered 765*f*, 765*s* shanks 762*f*, 762*s*. Tapering provides the surgeon with an improved view of the surgical field, especially in the area where the blades 115*f*, 115*s* contact the patient. This is especially useful when inserting the blades 115*f*, 115*s* between spinous processes.

FIG. 7C1 illustrates another embodiment 700C having releasable shanks 762*f*, 762*s*, similar to embodiment 700B; however, embodiment 700C includes rotatable handles 766*f*, 766*s* rotatably engaging corresponding shanks 762*f*, 762*s*. As used herein, rotatably engaging means that rotation of the handles 766*f*, 766*s* results in rotation of the vertical shanks 762*f*, 762*s*. The handles 766*f*, 766*s* are thus operable to rotate the blades 115*f*, 115*s* from the closed position shown in FIGS. 7C1 and 7C2 to the open position shown in FIG. 7C3 by drawing the handles 766*f*, 766*s* inward toward the arms 755*f*, 755*s*. The handles 766*f*, 766*s* thus provide the vertical shanks 762*f*, 762*s* with a range of angular motion comprising any combination of the following ranges: from 0° to 30°, 0° to 60°, 0° to 90°, 0° to 120°, 0° to 150°, and/or 0° to 180°. As shown in FIGS. 7C2 and 7C3 the handles 766*f*, 766*s* are retained within arm recesses 778*f*, 778*s* in the sides of the arms 755*f*, 755*s* using spring-loaded ball catches 770. Thus, the handles 766*f*, 766*s* snap into the arm recesses 778*f*, 778*s* but can still be easily removed from the recesses. The ball catches 770 comprise handle catches 776*f*, 776*s* and spring-loaded balls 774*f*, 774*s*. The spring may be, for instance and without limitation, a simple coil spring 769 (See FIG. 7D) housed within the arms 755*f*, 755*s*.

The embodiment 700C shown in FIGS. 7C1-7C3 enables a side-loading technique for retracting vertebrae. More specifically, with reference to FIGS. 7C4 and 7C5 the cusp 782 formed by the two blades of the embodiment 700C is shown being inserted 788A sideways between two spinous processes 786 of a spinal column 784, as indicated by motion arrows 788A. The handles 766*f*, 766*s* are then rotated back into the arms 755*f*, 755*s* thereby opening the blades 115*f*, 115*s* as indicated by motion arrows 788B. The vertebrae may then be retracted by rotating the knob through handle 745 counterclockwise. The ratchet 724 enables the blades 115*f*, 115*s* to be linearly displaced by precise increments inscribed on the rack 730 as shown in FIGS. 7C2-7C5. The increments are read through a window indicator 790 formed in the carrier 735.

FIG. 7D is a cross sectional view, taken along line 7D-7D of FIG. 7C3, illustrating the mechanical cooperation of the handles 766*f*, 766*s* with the arms 755*f*, 755*s* and shanks 762*f*, 762*s*. Although only the second handle 766*s*, second arm 755*s*, and second shank 762*s* are illustrated, the following description applies equally well to the first handle 766*f*, first arm 755*f*, and first shank 762*f*. The handle 766*s* is shown seated within arm recess 778*s*. The ball catch 770 is shown retaining the handle 766*s* within the arm recess 778*s*. More specifically, the spring loaded ball 744*s* is shown biased toward, and seated in, handle catch 776*s*. At the other end of the handle 766*s* is a handle linkage 767*s*, which engages socket 768*s* in a manner that fixes the orientation of the handle 766*s* relative to the handle linkage 767*s* such as, without limitation, an interference fit. The handle 766*s* and handle socket 768*s* cooperatively engage a shank 762*s* through a second spring-loaded ball catch comprising ball 744*s*2 and shank catch 776*s*2. An arm linkage 756*s* is shown cooperating with the handle linkage 767*s* to retain the handle 766*s*. The arm linkage 756*s* is in a clearance fit with the handle linkage 767*s* and the socket 768*s*. Thus, the handle 766*s*, socket 768*s*, and shank 762*s* are free to rotate as a unit about axis A-A while the arm 755*s* and arm linkage 756*s* remain stationary relative to the handle 766*s*. The person having ordinary skill in the art will readily understand that axis A-A is not a structural component of the embodiment, but rather is a mathematical abstraction.

FIG. 7E is a close up view of a portion of embodiment 700C illustrating how a shank 762*s* is received and retained by the embodiment. The shank 762*s* has an end portion 763*s* with a smaller diameter than the rest of the shank 762*s*. The diameter steps down at ledge 791*s*, thereby defining the end portion 763*s*. The end portion 763*s* includes a planar section 798*s* which cooperates with a flattened section 796*s* of the socket 768*s* to fix the orientation of the shank 762*s* relative to the socket 768*s*. The end portion 763*s* also includes elements of a ball catch for retaining the shank 762*s* in socket 768*s*. More specifically, the end portion 763*s* includes a shank catch 776*s*2 and a ball guide 794*s*. The spring-loaded ball is out of view in FIG. 7E but is shown in FIG. 7D as element 744*s*2. FIG. 7E illustrates one embodiment of the guide 794*s* wherein the guide has a semi paraboloid form. While the specific geometric form of the ball guide is not critical, the guide's form is intended to enable it to gradually compress the spring-loaded ball 744*s*2 into the handle 766*s*, which allows a user to install a shank with less force than would otherwise be required. In practice, the user inserts the end portion 763*s* of the shank into the socket 768*s* until the user feels the ball 744*s*2 click into the shank catch 776*s*2 and more or less simultaneously feels the socket 768*s* seat against the ledge 791*s*. The user can easily withdraw the shank 762*s* from the socket 768*s* by pulling the shank with sufficient force to overcome the spring-loaded ball catch.

FIG. 10 Illustrates an embodiment 1000 similar to embodiment 700C except that the arms 755*f*, 755*s* of embodiment 1000 are arcuately shaped 1002*s*, 1002*f* thereby providing an unobstructed view of the surgical field. FIGS. 11 and 12 further illustrate, from the user's perspective, how the arcuately shaped 1002*s*, 1002*f* arms 755*f*, 755*s* provide a clear view of the surgical field while inserting (FIG. 11) the blades 115*f*, 115*s* of embodiment 1000 between two spinous processes 1100, and while rotating (FIG. 12) the blades 115*f*, 115*s* around the spinous processes 1100. Similar to embodiment 700C, the blades 115*f*, 115*s* of embodiment 1000 are then spread apart by turning the knob using handle 745 counter clockwise 746. The specific arcuate geometry of the arms 755*f*, 755*s* is not critical and may take a variety of forms. Preferably, the arcs are opposed to each other as shown in FIG. 10, meaning the concave sides of the arcs 1002*f*, 1002*s* face each other, thereby providing an open view of the surgical field.

As shown in FIGS. 13 and 14, embodiment 1000 also differs from embodiment 700C in that it includes a latch 1004 for holding the pawl handle 520 of ratchet 724 in an engaged position. Accordingly, when engaged, the latch 1004 prevents the carrier 735 from moving in either direction. FIG. 14 is a close up view of the ratchet 724 mechanism of embodiment 1000. The ratchet includes a pawl 750 that is spring-biased toward a pinion gear 1402 so that it normally engages the pinion gear 1402 unless interrupted by the pawl handle 520. A coil spring 1404 is shown under the pawl handle 520. The coil spring is located within the carrier 735, engaging the carrier 735 on one end at the pawl handle 520 on the other end. The pawl handle 520 pivots on fulcrum 1400, thereby biasing the pawl 750 toward the pinion gear 1402.

With reference to FIG. 14, a latch 1004 is provided, comprising a latch pin 1406 and one or more latch receivers 1408. The latch can be configured to function in one of two modes. According to a first mode, the latch 1004 functions to lock the pawl 750 in engagement with the pinion gear 1402 thereby locking the ratchet 724 and fixing the linear displacement of the blades 115*f*, 115*s*. According to a second mode, the latch 1004 functions to hold the pawl 750 in disengagement from the pinion gear 1402, thereby allowing the carrier 735 to slide freely in either direction. The structural difference between the two modes amounts to the position of the receiver 1408 relative to the latch pin 1406 when the pawl handle 520 is depressed versus released. For instance, if the receiver 1408 is aligned with the latch pin 1406 when the pawl handle 520 is released, then depressing the latch button 1004 would lock the pawl 750 in engagement with the pinion gear 1402, corresponding to mode one. Alternatively, if the receiver 1408 is aligned with the latch pin 1406 when the pawl handle 520 is depressed then depressing the latch button 1004 would hold the pawl 750 in disengagement from the pinion gear 1402, corresponding two mode two.

Though not illustrated, the person having ordinary skill will readily understand that the ratchet 724 may be configured to selectively operate in either of these modes depending on the position of the pawl handle 520. For instance, such an embodiment would include two receivers 1408. A first receiver 1408 would align with the latch pin 1406 when the pawl handle 520 is depressed, and a second receiver 1408 would align with the latch pin 1406 when the pawl handle 520 is released. Thus, the user may select mode one or mode two by depressing the latch button 1004 while either depressing or releasing the pawl handle 520.

FIG. 8 illustrates the rack-and-pinion style retractor embodiment 700 of FIG. 7A in cooperation with a spinal column 800 from the point of view of the surgeon. As shown, a face 113*f* of the shank 112*f* does not extend beyond an inside face 103*i* of the straight first leg 102*f*. This arrangement of the shanks 112*f*, 112*s* at the ends 104*f*, 104*s* of the blades 115*f*, 115*s* keeps the shanks 112*f*, 112*s* clear of the surgical field and thus provides the surgeon with an unobstructed view. For convenience of illustration, the blades 115*f*, 115*s* appear to float near the spinous processes 802; however, in practice, the blades would abut the spinous processes thus providing a clear view of the surgical field.

The view shown in FIG. 8 is a top perspective with the retractor embodiment 700 positioned away from the viewer. This is typical of what a surgeon would see during use of an embodiment 700. The shanks 112*f*, 112*s* extend away from the user, placing the shank spreader 701 well outside the surgical field. Placing the shank spreader opposite the surgeon prevents the embodiment 700 from obstructing the surgeon's view and keeps the embodiment 700 out of the way of the surgeon's hands. FIG. 8 further illustrates an advantage of placing the shanks 112*f*, 112*s* at the ends 104*f*, 104*s* of the blades 115*f*, 115*s*. Namely, doing so places the shanks as far as possible from the surgeon's view of the surgical field. Another advantage is that the shanks 112*f*, 112*s* themselves function to longitudinally distract soft tissue which tends to eliminate the need for additional retractors, and thus further declutters the field.

FIG. 9 is an illustration of a rack and pinion-style retractor embodiment having a folding handle 745. The handle 745 is hingedly joined to the knob 740 through hinge 900. The handle 745 has a 90 degree range of motion about the hinge 900 relative to the knob 740. Such a handle 745 allows the surgeon to fold down the handle 745 once the retractor is positioned, thereby reducing the chance that the retractor may be inadvertently bumped or caught by another instrument.

Embodiments of the invention are well suited to implantation of stabilizing devices in non-fusion laminectomy procedures. For example, and without limitation, embodiments are suitable for retracting vertebrae during implantation of the Coflex® or Cofix® interlaminar stabilization device. In general terms, a Coflex® device is implanted through the posterior spine. An incision is made in the patient's back, and the space between the affected vertebrae is prepared by removing bone and ligament tissue to make room for the implant. A spacer is inserted between the vertebrae to estimate whether a proper fit will be attained. When the intervertebral space is prepared, the surgeon taps the Coflex® implant into position and crimps the device around the spinous processes. The foregoing procedure can be modified by using an embodiment of the invention to separate the diseased vertebrae. Bone and ligaments are then removed as usual, and the vertebrae are held in position with the retractor while the surgeon taps the implant into place.

Embodiments are also suitable for use in transforaminal lumbar interbody fusion (TLIF) procedures. Similar to the foregoing non-fusion procedure, the surgeon enters through the back of the spine. The diseased disc is partially removed and an implant is inserted into the interbody space to provide anatomical spacing between vertebrae and facilitate interbody fusion. Bone from the patient's pelvis, allograft bone, polyether ether ketone (PEEK), or titanium are utilized as implants. The implant is inserted to the interbody space, therefore facilitating fusion of vertebrae. Pedicel screws and rods are affixed to the back of the vertebrae to provide stabilization. Bone is also grafted to the hardware, forming a bone bridge that stabilizes the vertebrae. The foregoing procedure can be improved by using an embodiment of the invention to retract and hold the vertebrae in position while the spacer and hardware are implanted.

An embodiment of the invention is a spinous process oppositional or longitudinal retractor called the Carr Oppositional Retractor or "C.O.Retractor". The embodiment is specifically designed to be utilized during the implantation of nonfusion interlaminar procedures such as the Coflex® or Cofix® Interlaminar Stabilization devices. The embodiment is also designed for use in placement of lumbar interbody fusion devices as seen in a transforaminal lumbar interbody fusion (TLIF) procedure.

Coflex® and Cofix® are titanium implants surgically placed in the interlaminar segments of the lumbar spine to treat moderate to severe spinal stenosis. These implants are simple in concept, strong, and flexible enough to mimic normal spine biomechanics and thus "restore" normal movement versus fusion instrumentation designed to "restrict" normal movement.

TLIF implant devices are designed to facilitate lumbar interbody fusion. In order to implant nonfusion interlaminar devices or TLIF implants, a posterior approach to the spine through the skin, posterior lumbar fascia and muscular attachments is performed. Once direct visualization of the posterior spine is achieved, removal of the interspinous ligament and appropriate portions of the laminae allows the placement of C.O.Retractor.

Utilizing a longitudinal rack and pinion type oppositional retractor, the C.O.Retractor generally includes a pair of arms that are opposite to each other. At the end of the arms of retraction, there are two downward 90 degree arms of 25 mm to 100 mm in length. Attached to the inferiorly directed arms are the C.O.Retractor U-shaped blades, as described in more detail supra. These blades dock to the spinous processes of the patient and may be sized to fit both men and women of all shapes and sizes. The particular design of the C.O.Retractor U-shaped oppositional blades attached to the inferiorly angled 90 degree arms places the arms on the opposite side of the spinous process away from the surgeon. This allows better visualization for the surgeon working in the microscope as well as improved longitudinal tissue retraction.

The subsequent longitudinal retraction of the spinous processes further exposes the interlaminar space and makes the ligamentum flavum taut. The improved interlaminar visualization and tension of the ligamentum flavum allows safer and easier surgical removal of compressive tissues.

The C.O.Retractor also greatly facilitates placement of lumbar interbody fusion devices as seen in a transforaminal lumbar interbody fusion or (TLIF) procedure.

Prior to placing the C.O.Retractor, the "Method of Insertion" of the retractor comprises preparation of the spinous processes to optimize the docking of the retractor. The preparation of the spinous processes to accept the C.O.Retractor will allow interlaminar devices such as the Coflex® or Cofix® to be implanted more easily at the end of the surgery.

The preparation of the spinous process to accept C.O.Retractor will decrease the surgical time as it improves visualization. The retractor U-Shaped blades are also the same size as the Coflex® or Cofix® implants so no further carpentry is required.

The C.O.Retractor is specifically designed for both non-fusion interlaminar devices such as Coflex® or Cofix®, as well as TLIF interbody fusion surgeries.

The C.O.Retractor is beneficial to all surgeons who perform laminectomy, nonfusion interlaminar surgeries and TLIF surgeries as it improves the direct visualization of the neural compressive elements that need to be removed. The C.O.Retractor decreases surgical time as well as time under anesthesia for patients, thus directly improving surgical outcomes for patients.

With reference to FIGS. 11-14, a minimally invasive unilateral side-loading method of insertion of embodiments having blades with beveled free ends is as follows. Side-loading embodiments are introduced on one side of the spinous processes and therefore reduces the tissue trauma and dissection of muscles necessary for a spine surgery. Such embodiments may also be utilized in procedures that require bilateral removal or decompression of compressive tissues such as ligaments, bone, or herniated disc material.

With particular reference to FIGS. 11 and 12, the surgeon visualizes the surgical field through the opening 1200 provided by the arcuately shaped 1002*f*, 1002*s* arms 755*f*, 755*s*. The beveled free ends 108*f*, 108*s* of the blades 115*f*, 115*s* are inserted through the interspinous ligament tissue (not shown), piercing the interspinous ligament, and thereby making an opening (not shown) between the spinous processes 1100. Optionally, the surgeon may engage the latch 1004 of the ratchet 724, thereby holding the pawl 750 in disengagement from the pinion gear, and allowing the carrier 735 to slide freely on the rack 730. Then, as shown in FIG. 12, the shanks 762*f*, 762*s* are rotated using the scissor-like handles 766*f*, 766*s*. This rotates the blades 115*f*, 115*s* securely around the spinous processes, fully engaging them and preventing abnormal rotation. If the surgeon chooses to allow the carrier 735 to slide freely, the carrier may slide while rotating the blades 115*f*, 115*s*. The surgeon would release the latch 1004 at this point, reengaging the ratchet 724. Once the blades 115*f*, 115*s* are seated in contact with the spinous processes 1100 and rotated into their fully engaged position, a distraction is performed by turning handle 745 counterclockwise to spread the retractor blades. As the handle 745 is turned the ratchet 724 clicks as the pawl 750 engages the next cog of the pinion gear 1402, providing audible and tactile feedback to the surgeon. See FIG. 14. Furthermore, advancing the pawl 750 from cog to cog corresponds to an accurately measured linear movement of the blades 115*f*, 115*s*. According to one embodiment one click corresponds to 1 mm of linear movement of the blades 115*f*, 115*s*. With reference to FIG. 13, the provided window indicator 790 displays the linear displacement of the blades 115*f*, 115*s*. For instance, the illustrated embodiment displays numerals inscribed on the underlying rack 730 through the window indicator 790. The rack may be inscribed with regularly spaced numerals and/or regularly spaced hash marks, providing a measure of linear displacement readable through the indicator window 790. The displayed numeral corresponds to linear displacement in millimeters. Having a readout of linear displacement enables the surgeon to size the interspinous space as needed to accurately place various implantable devices. Thus, the surgeon can cease actuating the shank spreader 701, i.e. can cease turning the handle 745, when the window indicator shows, or "indicates", a predetermined degree of distraction. Optionally, the surgeon may engage the latch 1004 of the ratchet 724, thereby locking the pawl 750 in engagement with the pinion gear, and preventing the carrier 735 from moving. Thus the blades 115*f*, 115*s* can be locked in fixed linear displacement, leaving the surgeon's hands free for other tasks. Furthermore the opening 1200 provided by the arcuately shaped 1002*f*, 1002*s* arms 755*f*, 755*s* provides the surgeon with a considerably larger view of the surgical field than would otherwise be available.

It will be apparent to those skilled in the art that the above methods and apparatuses may be changed or modified without departing from the general scope of the invention. The invention is intended to include all such modifications and alterations insofar as they come within the scope of the appended claims or the equivalents thereof. Moreover, while the examples discussed herein and illustrated in the figures combine certain inventive features, embodiments of the invention are not limited to the particular combinations described. For example, and without limitation, embodiments of the invention also include retractors having vertical shanks that are rotatable with scissor-like handles 766*f*, 766*s* but lack a means for releasing the shanks. Any combination of the features described herein that would be obvious to the person having skill in the art, are within the scope of the present invention.

I claim:

1. A spinal retractor blade (115), comprising:

a straight first leg (102) having an end (104) joined to an end (118) of a shank (112), wherein the straight first leg is greater than 0 cm and less than or equal to 6.0 cm in length;

a straight second leg (106) having a free end (108), the straight second leg (106) oriented 0° relative to the straight first leg (102), wherein the straight second leg is greater than 0 cm and less than or equal to 6.0 cm in length; and a transition (114) from the straight first leg (102) to the straight second leg (106), wherein a minimum width ($w_{min}$) between the straight first leg (102) and the straight second leg (106) is operable to receive a spinous process.

2. The spinal retractor blade of claim 1, wherein the end (104) of the straight first leg (102) is joined to the end (118) of the shank (112) so that a face (113) of the shank (112) does not extend beyond an inside face (103*i*) of the straight first leg (102).

3. The spinal retractor blade of claim 1, wherein the transition (114) is arcuate.

4. The spinal retractor blade of claim 1, wherein a length of the straight second leg (106) is determined by a length (L1) of the blade exceeding a distance between a tangent line (T) of an apex (116) of the transition (114) and a parallel line drawn through an end of the straight second leg (106) most proximal to the tangent line (T) and an end of the straight first leg (102) most proximal to the tangent line (T), wherein the length of the straight second leg (106) does not exceed 6.0 cm.

5. The spinal retractor blade of claim 1, wherein the blade comprises a band (400) having a height (h) from about 4.0 cm to about 0.3 cm+/−10%.

6. The spinal retractor blade of claim 1, wherein the straight first leg (102) and the straight second leg (106) are spaced apart by the minimum width ($w_{min}$) from about 0.3 cm to about 2.0 cm+/−10%.

7. The spinal retractor blade of claim 1, wherein the free end (108) of the straight second leg (106) is beveled.

8. The spinal retractor blade of claim 1, wherein the straight first leg (102) is oriented relative to the straight second leg (106) at an angle between 0° and 45° from parallel.

* * * * *